United States Patent
Tokunaga et al.

(10) Patent No.: US 11,229,594 B2
(45) Date of Patent: Jan. 25, 2022

(54) OIL-IN-WATER EMULSION COMPOSITION

(71) Applicant: L'OREAL, Paris (FR)

(72) Inventors: Emiko Tokunaga, Toyko (JP); Hiroko Abe, Kawasaki (JP)

(73) Assignee: L'OREAL, Paris (FR)

(*) Notice: Subject to any disclaimer, the term of this patent is extended or adjusted under 35 U.S.C. 154(b) by 218 days.

(21) Appl. No.: 15/738,711

(22) PCT Filed: Aug. 5, 2016

(86) PCT No.: PCT/JP2016/073810
§ 371 (c)(1),
(2) Date: Dec. 21, 2017

(87) PCT Pub. No.: WO2017/030106
PCT Pub. Date: Feb. 23, 2017

(65) Prior Publication Data
US 2018/0168992 A1    Jun. 21, 2018

(30) Foreign Application Priority Data
Aug. 18, 2015   (JP) .............................. JP2015-160864

(51) Int. Cl.
| A61Q 19/00 | (2006.01) |
| A61K 8/90 | (2006.01) |
| A61K 8/04 | (2006.01) |
| A61K 8/81 | (2006.01) |
| A61K 8/06 | (2006.01) |
| A61Q 1/00 | (2006.01) |
| A61K 8/34 | (2006.01) |
| A61K 8/60 | (2006.01) |
| C08L 33/24 | (2006.01) |
| C08L 33/26 | (2006.01) |

(52) U.S. Cl.
CPC ............ *A61K 8/8158* (2013.01); *A61K 8/062* (2013.01); *A61K 8/345* (2013.01); *A61K 8/608* (2013.01); *A61K 8/8194* (2013.01); *A61K 8/90* (2013.01); *A61Q 1/00* (2013.01); *A61Q 19/00* (2013.01); *C08L 33/24* (2013.01); *C08L 33/26* (2013.01); *A61K 2800/10* (2013.01); *A61K 2800/48* (2013.01); *A61K 2800/548* (2013.01); *A61K 2800/594* (2013.01); *C08L 2201/52* (2013.01); *C08L 2205/025* (2013.01)

(58) Field of Classification Search
CPC .............. A61Q 1/00; A61K 8/31; A61K 8/04
See application file for complete search history.

(56) References Cited

U.S. PATENT DOCUMENTS

| 2005/0175648 A1 | 8/2005 | De La Poterie et al. |
| 2005/0180936 A1 | 8/2005 | Pays |
| 2010/0031969 A1* | 2/2010 | Jager Lezer ......... A45D 40/262 132/200 |
| 2011/0217253 A1* | 9/2011 | Arnaud .................. A61K 8/064 424/63 |
| 2013/0171084 A1* | 7/2013 | Kawaratani .............. A61K 8/89 424/64 |
| 2015/0147363 A1* | 5/2015 | Perez-Nowak ...... A61Q 19/001 424/401 |

FOREIGN PATENT DOCUMENTS

| EP | 1 552 806 A1 | 7/2005 |
| EP | 2 448 757 A1 | 5/2012 |
| JP | 04-243842 A | 8/1992 |
| JP | 2000-119124 A | 4/2000 |
| JP | 2005-132821 A | 5/2005 |
| JP | 2005-225867 A | 8/2005 |
| JP | 2007-506708 A | 3/2007 |
| KR | 10-2004-0027429 A | 4/2004 |
| KR | 10-2015-0023844 A | 3/2015 |
| WO | 00/49997 A1 | 8/2000 |
| WO | 2005/030158 A1 | 4/2005 |
| WO | 2011002986 A1 | 1/2011 |

OTHER PUBLICATIONS

International Search Report for PCT/JP2016/073810, dated Feb. 11, 2016.
International Search Report for PCT/JP2016/073810, dated Nov. 2, 2016.
Korean Office Action for Application No. 10-2017-7036914, dated Mar. 11, 2019 with translation.
Japanese Office Action for Application No. 2018-508258, dated Mar. 25, 2019 with translation.
Translated Notice of Allowance for counterpart Application No. 10-2017-7036914, dated Feb. 20, 2020.

\* cited by examiner

*Primary Examiner* — Kyle A Purdy
(74) *Attorney, Agent, or Firm* — The Marbury Law Group, PLLC

(57) ABSTRACT

The present invention relates to a composition in the form of an O/W emulsion, comprising: (a) at least one hydrocarbon-based block copolymer comprising at least one styrene block and at least one block comprising units chosen from butadiene, ethylene, propylene, butylene and isoprene or a mixture thereof, which are optionally hydrogenated; (b) at least one film-forming linear ethylenic polymer devoid of styrene; (c) at least one oil; and (d) water. The composition according to the present invention can maintain the form of an O/W emulsion for a long period of time, and can exhibit good cosmetic properties such as soft feeling to the touch, uniform adhesion to the skin and long lasting cosmetic effects.

11 Claims, 1 Drawing Sheet

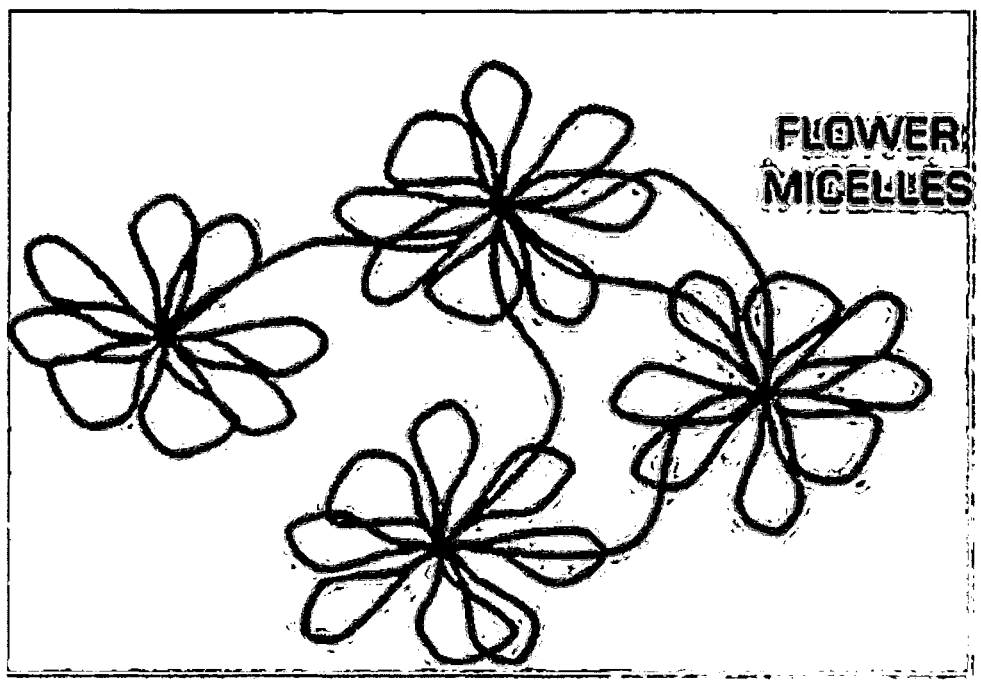

OIL-IN-WATER EMULSION COMPOSITION

CROSS REFERENCE TO RELATED APPLICATIONS

This is a national stage application of PCT/EP2016/073810, filed internationally on Aug. 5, 2016, which claims priority to Japanese Application No. 2015-160864, filed on Aug. 18, 2015, both of which are incorporated by reference herein in their entireties.

TECHNICAL FIELD

The present invention relates to a composition in the form of an oil-in-water (O/W) emulsion, more particularly to a cosmetic composition for making up and/or caring for the skin.

BACKGROUND ART

It is known practice, in the cosmetics or dermatological field, to use O/W emulsions. These emulsions which consist of a fatty phase dispersed in an aqueous phase have an external aqueous phase, and therefore cosmetic/dermatological products based on the O/W emulsions are pleasant to use due to the feeling of freshness that the external aqueous phase can provide.

DISCLOSURE OF INVENTION

However, O/W emulsions are, in general, weak to sweat and moisture due to rain and humidity in the air because the outer phase of the emulsions substantially consists of water, and therefore, it tends to be difficult for the O/W emulsions to stay on the skin for a long period of time. Thus, it is often difficult for cosmetic compositions based on O/W emulsions to provide long lasting cosmetic effects.

Further, it is preferable that O/W emulsions are stable over time without phase separation. Furthermore, it is also preferable for O/W emulsions to provide good cosmetic effects such as soft feeling to the touch of a cosmetic film, uniform adhesion to the skin, and long lasting cosmetic effects, if they are used as cosmetic compositions.

An objective of the present invention is to provide a composition in the form of an O/W emulsion, which is stable over time, while providing good cosmetic properties such as soft feeling to the touch, uniform adhesion to the skin and long lasting cosmetic effects.

The above objective can be achieved by a composition in the form of an O/W emulsion, comprising:
(a) at least one hydrocarbon-based block copolymer comprising at least one styrene block and at least one block comprising units chosen from butadiene, ethylene, propylene, butylene and isoprene or a mixture thereof, which are optionally hydrogenated;
(b) at least one film-forming linear ethylenic polymer devoid of styrene;
(c) at least one oil; and
(d) water.

The (a) hydrocarbon-based block copolymer may comprise at least one styrene block and at least one block comprising units chosen from butadiene, ethylene, propylene, butylene and isoprene or a mixture thereof.

The (a) hydrocarbon-based block copolymer may be chosen from styrene-ethylene/propylene, styrene-ethylene/butadiene, styrene-ethylene/butylene diblock copolymers, which are optionally hydrogenated, and styrene-ethylene/propylene-styrene, styrene-ethylene/butadiene-styrene, styrene-isoprene-styrene and styrene-butadiene-styrene triblock copolymers, which are optionally hydrogenated, and mixtures thereof.

It is preferable that the (a) hydrocarbon-based block copolymer be a hydrogenated styrene/butadiene copolymer, a hydrogenated styrene/isoprene copolymer, or a mixture thereof.

The (a) hydrocarbon-based block copolymer may be present in the composition in a content ranging from 0.01% to 10% by weight, preferably ranging from 0.05% to 5% by weight, and more preferably from 0.1 to 2% by weight, relative to the total weight of the composition.

It is preferable that the (b) film-forming linear ethylenic polymer comprise at least one first block and at least one second block having different glass transition temperatures (Tg), said first and second blocks being connected to one another via an intermediate block comprising at least one constituent monomer of the first block and at least one constituent monomer of the second block.

The first block may be chosen from:
i) a block having a Tg of greater than or equal to 40° C.,
ii) a block having a Tg of less than or equal to 20° C.,
iii) a block having a Tg of between 20 and 40° C., and
the second block is chosen from category i), or iii) different from the first block.

The monomers, the homopolymer of which has a glass transition temperature of greater than or equal to 40° C., may be chosen from the following monomers:
methacrylates of formula $CH_2=C(CH_3)-COOR_1$, in which $R_1$ represents a linear or branched unsubstituted alkyl group containing from 1 to 4 carbon atoms, such as a methyl, ethyl, propyl or isobutyl group or $R_1$ represents a $C_4$ to $C_{12}$ cycloalkyl group, preferably a $C_8$ to $C_{12}$ cycloalkyl, such as isobornyl methacrylate;
acrylates of formula $CH_2=CH-COOR_2$, in which $R_2$ represents a $C_4$ to $C_{12}$ cycloalkyl group, such as isobornyl acrylate, or a tert-butyl group;
(meth)acrylamides of formula:

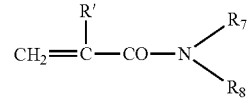

where $R_7$ and $R_8$, which are identical or different, each represent a hydrogen atom or a linear or branched alkyl group of 1 to 12 carbon atoms, such as an n-butyl, t-butyl, isopropyl, isohexyl, isooctyl or isononyl group, or $R_7$ represents H and $R_8$ represents a 1,1-dimethyl-3-oxobutyl group, and R' denotes H or methyl; and
their mixtures.

The monomers, the homopolymer of which has a glass transition temperature of less than or equal to 20° C., may be chosen from the following monomers:
acrylates of formula $CH_2=CHCOOR_3$, $R_3$ representing a linear or branched $C_1$ to $C_{12}$ unsubstituted alkyl group, with the exception of the tert-butyl group, in which one or more heteroatoms chosen from O, N or S is (are) optionally inserted;
methacrylates of formula $CH_2=C(CH_3)-COOR_4$, $R_4$ representing a linear or branched $C_6$ to $C_{12}$ unsubstituted alkyl group, with the exception of the tert-butyl group, in which one or more heteroatoms chosen from O, N and S is (are) optionally inserted;

vinyl esters of formula $R_5$—CO—O—CH—$CH_2$, where $R_5$ represents a linear or branched $C_4$ to $C_{12}$ alkyl group, $C_4$ to $C_{12}$ alkyl groups;

$C_4$ to $C_{12}$ alkyl vinyl ethers;

N—($C_4$ to $C_{12}$ alkyl)acrylamides, such as N-octylacrylamide, and their mixtures.

The first block and/or the second block may comprise at least one additional monomer.

The additional momomer may be chosen from:

monomers with ethylenic unsaturation(s) comprising at least one carboxylic or sulfonic acid functional group, ethylenically unsaturated monomers comprising at least one tertiary amine function, such as 2-vinylpyridine, 4-vinylpyridine, dimethylaminoethyl methacrylate, diethylaminoethyl methacrylate, dimethylaminopropylmethacrylamide, and salts thereof, the methacrylates of formula $CH_2=C(CH_3)$—$COOR_6$ in which $R_6$ represents a linear or branched alkyl group containing from 1 to 4 carbon atoms, such as a methyl, ethyl, propyl or isobutyl group, the said alkyl group being substituted with one or more substituents chosen from hydroxyl groups (for instance, 2-hydroxypropyl methacrylate and 2-hydroxyethyl methacrylate) and halogen atoms (Cl, Br, I or F), such as trifluoroethyl methacrylate, the methacrylates of formula $CH_2=C(CH_3)$—$COOR_9$, $R_9$ representing a linear or branched $C_6$ to $C_{12}$ alkyl group in which one or more heteroatoms chosen from O, N and S are optionally intercalated, the said alkyl group being substituted with one or more substituents chosen from hydroxyl groups and halogen atoms (Cl, Br, I or F), the acrylates of formula $CH_2=CHCOOR_{10}$, $R_{10}$ representing a linear or branched $C_1$ to $C_{12}$ alkyl group substituted with one or more substituents chosen from hydroxyl groups and halogen atoms (Cl, Br, I and F), such as 2-hydroxypropyl acrylate and 2-hydroxyethyl acrylate, or $R_{10}$ represents a $C_1$ to $C_{12}$ alkyl-O-POE (polyoxyethylene) with repetition of the oxyethylene unit 5 to 10 times, for example, methoxy-POE, or $R_8$ represents a polyoxyethylenated group comprising from 5 to 10 ethylene oxide units, and their mixtures.

It is preferable that the (b) film-forming linear ethylenic polymer devoid of styrene be acrylic acid/isobutyl acrylate/isobornyl acrylate copolymer.

The (b) film-forming linear ethylenic polymer devoid of styrene may be present in the composition in a content ranging from 0.01% to 10% by weight, preferably ranging from 0.05% to 5% by weight, and more preferably from 0.1 to 2% by weight, relative to the total weight of the composition.

The (c) oil may be present in the composition in a content ranging from 0.1% to 20% by weight, preferably ranging from 0.5 to 15% by weight, and more preferably from 1 to 10% by weight, relative to the total weight of the composition.

The composition according to the present invention may further comprise (e) at least one hydrophilic thickener.

The composition according to the present invention may also comprise (f) at least one associative polymer.

BRIEF DESCRIPTION OF DRAWINGS

FIG. 1 shows a front view of an example of a network formed by an associative polyurethane thickener in water in which the hydrophobic parts of the associative polyurethane thickener connects to form quasi-micelles which are indicated as flower micelles.

BEST MODE FOR CARRYING OUT THE INVENTION

After diligent research, the inventors have discovered that it is possible to provide a composition in the form of an O/W emulsion, which is stable over time, while providing good cosmetic properties such as soft feeling to the touch, uniform adhesion to the skin and long lasting cosmetic effects.

Thus, the composition according to the present invention is in the form of an O/W emulsion, and comprises:

(a) at least one hydrocarbon-based block copolymer;

(b) at least one film-forming linear ethylenic polymer devoid of styrene comprising at least one styrene block and at least one block comprising units chosen from butadiene, ethylene, propylene, butylene and isoprene or a mixture thereof, which are optionally hydrogenated;

(c) at least one oil; and (d) water.

The term "O/W emulsion" or "oil-in-water emulsion" means any macroscopically homogeneous composition comprising a continuous aqueous phase and a fatty phase dispersed in the said aqueous phase in the form of droplets.

The composition according to the present invention can maintain the form of an O/W emulsion for a long period of time, and can exhibit good cosmetic properties such as soft feeling to the touch, uniform or homogeneous adhesion to the skin and long lasting cosmetic effects. The composition according to the present invention may further provide a fresh moist sensation.

If the composition according to the present invention further includes (f) at least one associative polymer, the composition can further enhance cosmetic effects such as smooth applicability without forming noodles, uniform spreadability, and ease of dispensing specific amount of the composition from a container including the composition.

The composition according to the present invention may appear to be a gel.

Hereafter, each of the compositions according to the present invention will be described in a detailed manner

[Hydrocarbon-Based Block Copolymer]

The composition according to the present invention includes at least one (a) hydrocarbon-based block copolymer. If two or more (a) hydrocarbon-based block copolymers are used, they may be the same or different.

It is preferable that the (a) hydrocarbon-based block copolymer be soluble or dispersible in a liquid fatty phase as defined later.

It is preferable that the (a) hydrocarbon-based block copolymer be capable of thickening or gelling the fatty phase of the composition according to the present invention. Thus, it is preferable that the (a) hydrocarbon-based block copolymer used in the composition according to the present invention can function as a polymeric gelling agent.

It is preferable that the (a) hydrocarbon-based block copolymer be an amorphous polymer. The term "amorphous polymer" means a polymer that does not have a crystalline form. The (a) hydrocarbon-based block copolymer is also preferably film-forming, i.e. it is capable of forming a film when applied to the skin and the like.

The (a) hydrocarbon-based block copolymer may especially be a diblock, triblock, multiblock, radial or star copolymer, or mixtures thereof.

Such hydrocarbon-based block copolymers are described in patent application US-A-2002/005 562 and in patent U.S. Pat. No. 5,221,534.

The (a) hydrocarbon-based block copolymer may contain at least one block whose glass transition temperature is preferably less than 20° C., preferably less than or equal to 0° C., preferably less than or equal to −20° C. and more preferably less than or equal to −40° C. The glass transition temperature of the said block may be between −150° C. and 20° C. and especially between −100° C. and 0° C.

It is preferable that the (a) hydrocarbon-based block copolymer used in the composition according to the present invention be an amorphous copolymer formed by polymerization of olefins.

The (a) hydrocarbon-based block copolymer comprises at least a styrene monomer (i.e., is obtained from at least a styrene monomer).

Advantageously, the (a) hydrocarbon-based block copolymer may be an amorphous block copolymer of styrene and of specific olefin(s).

Thus, the (a) hydrocarbon-based block copolymer comprises at least one styrene block and at least one block comprising units chosen from butadiene, ethylene, propylene, butylene and isoprene or a mixture thereof.

According to one preferred embodiment, the (a) hydrocarbon-based block copolymer is hydrogenated to reduce the residual ethylenic unsaturations after the polymerization of the monomers.

In particular, the (a) hydrocarbon-based block copolymer is a copolymer, optionally hydrogenated, containing styrene blocks and ethylene/$C_3$-$C_4$ alkylene blocks.

According to one preferred embodiment, the (a) hydrocarbon-based block copolymer used in the composition according to the present invention may be a diblock copolymer, which is preferably hydrogenated, preferably chosen from styrene-ethylene/propylene copolymers, styrene-ethylene/butadiene copolymers and styrene-ethylene/butylene copolymers.

According to one embodiment of the present invention, a linear diblock copolymer based on styrene and ethylene/propylene, a butylene/ethylene/styrene copolymer, or a hydrogenated styrene/isoprene copolymer is preferable as the (a) hydrocarbon-based block copolymer. Such a diblock copolymer is especially sold under the name Kraton® G1701E by the company Kraton Polymers.

According to another preferred embodiment, the (a) hydrocarbon-based block copolymer used in the composition according to the present invention may be a triblock copolymer, which is preferably hydrogenated, preferably chosen from styrene-ethylene/propylene-styrene copolymers, styrene-ethylene/butadiene-styrene copolymers, styrene-isoprene-styrene copolymers and styrene-butadiene-styrene copolymers. Triblock polymers are especially sold under the names Kraton® G1650, Kraton® G1652, Kraton® D1101, Kraton® D1102 and Kraton® D1160 by the company Kraton Polymers.

According to one embodiment of the present invention, the (a) hydrocarbon-based block copolymer may be a linear styrene-ethylene/butylene-styrene triblock copolymer or a hydrogenated styrene/butadiene copolymer. Such as triblock copolymer is especially sold under the name Kraton® G1657M by the company Kraton Polymers.

According to one preferred embodiment of the invention, it is especially possible to use, as the (a) hydrocarbon-based block copolymer, a mixture of a styrene-ethylene/butylene-styrene triblock copolymer and of a styrene-ethylene/butylene diblock copolymer.

According to another preferred embodiment, the composition according to the present invention may comprise, as the (a) hydrocarbon-based block copolymer, a mixture of styrene-butylene/ethylene-styrene hydrogenated triblock copolymer and of ethylene-propylene-styrene hydrogenated star polymer, such a mixture possibly being especially in isododecane or in another oil. Such mixtures are sold, for example, by the company Penreco under the trade names Versagel® M5960 and Versagel® M5670.

Advantageously, a diblock copolymer such as those described previously is used as a polymeric gelling agent, in particular a styrene-ethylene/propylene diblock copolymer or a mixture of diblock and triblock copolymers, as described previously.

The (a) hydrocarbon-based block copolymer may be present in the composition in a content ranging from 0.01% to 10% by weight, preferably ranging from 0.05 to 5% by weight, and more preferably from 0.1 to 2% by weight, relative to the total weight of the composition.

[Film-Forming Linear Ethylenic Polymer Devoid of Styrene]

The composition according to the present invention includes at least one (b) film-forming ethylenic polymer devoid of styrene. If two or more (b) film-forming ethylenic polymers devoid of styrene are used, they may be the same or different.

The (b) film-forming ethylenic polymer devoid of styrene is different from the (a) hydrocarbon-based block copolymer explained above.

The term "ethylenic" polymer means a polymer obtained by polymerization of ethylenically unsaturated monomers.

The term "film-forming" polymer means a polymer capable of forming, by itself or in the presence of an auxiliary film-forming agent, a continuous and adherent film on a support, particularly on keratin materials such as skin.

The (b) film-forming ethylenic polymer devoid of styrene does not include a styrene unit. By a polymer free from styrene units is meant a polymer containing less than 10%, preferably less than 5%, preferably less than 2%, more preferably less than 1% by weight, and even more preferably 0% by weight i) of a styrene unit of formula —$CH(C_6H_5)$—$CH_2$— or ii) of a substituted styrene unit, for example methylstyrene, chlorostyrene or chloromethylstyrene.

According to one embodiment, the (b) film-forming ethylenic polymer devoid of styrene may be obtained from aliphatic ethylenic monomers. By aliphatic monomer is meant a monomer containing no aromatic group.

According to one embodiment, the (b) film-forming ethylenic polymer devoid of styrene may be an ethylenic polymer obtained from aliphatic ethylenic monomers comprising a carbon-carbon double bond and at least one ester group —COO— or amide group —CON—. The ester group may be bonded to one of the two unsaturated carbons via the carbon atom or the oxygen atom. The amide group may be bonded to one of the two unsaturated carbons via the carbon atom or the nitrogen atom.

According to one embodiment, the (b) film-forming ethylenic polymer devoid of styrene is a linear polymer. By opposition, a polymer having a non-linear structure is, for example, a polymer having a branched, starburst, graft or other structure.

It is preferable that the (b) film-forming ethylenic polymer devoid of styrene be a non-elastomeric polymer.

The term "non-elastomeric polymer" is understood to mean a polymer which, when it is subjected to a stress targeted at drawing it (for example by 30% relative to its initial length), does not return to a length substantially identical to its initial length when the stress ceases.

More specifically, the term "non-elastomeric polymer" denotes a polymer having an instantaneous recovery $R_i<50\%$ and a delayed recovery $R_{2h}<70\%$ after having undergone an elongation of 30%. Preferably, $R_i$ is <30% and $R_{2h}<50\%$.

More specifically, the non-elastomeric nature of the polymer is determined according to the following protocol:

A polymer film is prepared by pouring a solution of the polymer into a Teflon-treated matrix and then drying for 7 days in surroundings controlled at 23±5° C. and 50±10% relative humidity.

A film with a thickness of approximately 100 μm is then obtained, from which rectangular test specimens with a width of 15 mm and a length of 80 mm are cut (for example with a hollow punch).

A tensile stress is applied to the sample using a device sold under the Zwick reference, under the same temperature and humidity conditions as for the drying.

The test specimens are drawn at a rate of 50 mm/min and the distance between the clamping jaws is 50 mm, which corresponds to the initial length ($I_0$) of the test specimen.

The instantaneous recovery $R_i$ is determined in the following way:
  the test specimen is drawn by 30% ($\varepsilon_{max}$), that is to say approximately 0.3 times its initial length ($I_0$), and
  the stress is released by applying a return rate equal to the tensioning rate, i.e. 50 mm/min, and the residual elongation of the test specimen is measured as a percentage, after returning to zero stress ($\varepsilon_i$).

The instantaneous recovery in % ($R_i$) is given by the formula below: $R_{i=(\varepsilon max-\varepsilon i)/\varepsilon max}*100$ To determine the delayed recovery, the residual elongation of the test specimen is measured as a percentage ($\varepsilon_{2h}$).

The delayed recovery in % ($R_{2h}$) is given by the formula below: $R_{2h =(\varepsilon max-\varepsilon 2h)/\varepsilon max}*100$ Purely by way of indication, the (b) film-forming ethylenic polymer devoid of styrene used according to an embodiment of the present invention may have an instantaneous recovery $R_i$ of 10% and a delayed recovery $R_{2h}$ of 30%.

The polydispersity index I of a polymer is equal to the ratio of the weight-average mass Mw to the number-average mass Mn.

The weight-average molar masses (Mw) and the number-average molar masses (Mn) are determined by gel permeation liquid chromatography (solvent THF, calibration curve drawn up with linear polystyrene standards, refractometric detector).

The weight-average mass (Mw) of the (b) film-forming ethylenic polymer devoid of styrene used in the composition according to the present invention may preferably be less than or equal to 300 000, it ranges, for example, from 35 000 to 200 000 and better still from 45 000 to 150 000.

The number-average mass (Mn) of the (b) film-forming ethylenic polymer devoid of styrene used in the composition according to the present invention may preferably be less than or equal to 70 000, it ranges, for example, from 10 000 to 60 000 and better still from 12 000 to 50 000.

The polydispersity index of the (b) film-forming ethylenic polymer devoid of styrene used in the composition according to the present invention may be greater than 2, for example is greater than 2 and less than or equal to 9, preferably greater than or equal to 2.5, for example ranging from 2.5 to 8, and better still greater than or equal to 2.8, in particular from 2.8 to 6.

The (b) film-forming ethylenic polymer devoid of styrene may be a block polymer. By a "block" polymer is meant a polymer comprising at least 2 distinct blocks, preferably at least 3 distinct blocks.

According to one mode of implementation, the (b) film-forming ethylenic polymer devoid of styrene may comprise at least one first block and at least one second block. By "at least" one block is meant one or more blocks. It is specified that, in the text above and below, the terms "first" and "second" blocks in no way condition the order of the said blocks (or sequences) in the structure of the polymer.

According to one mode of implementation, the (b) film-forming ethylenic polymer devoid of styrene may comprise at least one first block and at least one second block which have different glass transition temperatures (Tg).

In this mode of implementation, the first and second blocks may be connected to one another by an intermediate segment having a glass transition temperature between the glass transition temperatures of the first and second blocks.

According to one mode of implementation, the (b) film-forming ethylenic polymer devoid of styrene may comprise at least one first block and at least one second block connected to one another by an intermediate segment comprising at least one constituent monomer of the first block and at least one constituent monomer of the second block.

Thus, it is preferable that the (b) film-forming linear ethylenic polymer comprise at least one first block and at least one second block having different glass transition temperatures (Tg), said first and second blocks being connected to one another via an intermediate block comprising at least one constituent monomer of the first block and at least one constituent monomer of the second block.

Preferably, the intermediate block may be obtained essentially from constituent monomers of the first block and of the second block. By "essentially" is meant to an extent of at least 85%, preferably at least 90%, more preferably 95% and more preferably still 100%.

Advantageously, the intermediate segment comprising at least one constituent monomer of the first block and at least one constituent monomer of the second block of the polymer is a random polymer.

According to one mode of implementation, the (b) film-forming ethylenic polymer devoid of styrene may comprise at least one first block and at least one second block which are incompatible with one another in the organic liquid medium of the composition of the present invention. By "blocks incompatible with one another" is meant that the mixture formed from the polymer corresponding to the first block and from the polymer corresponding to the second block is not miscible in the organic liquid that is in a majority by weight in the organic liquid medium of the composition, at ambient temperature (25° C.) and atmospheric pressure ($10^5$ Pa), for a polymer mixture content greater than or equal to 5% by weight, relative to the total weight of the mixture (polymers and majority organic liquid), with the provisos that
i) the said polymers are present in the mixture in an amount such that the respective weight ratio ranges from 10/90 to 90/10, and that
ii) each of the polymers corresponding to the first and second blocks has an average molecular mass (by weight or by number) equal to that of the block polymer +/−15%.

In the case where the organic liquid medium comprises a mixture of organic liquids, should two or more liquids be present in identical mass proportions, the said polymer mixture is not miscible in at least one of them.

In the case where the organic liquid medium comprises a single organic liquid, the said liquid, quite obviously, constitutes the liquid that is in a majority by weight.

By "organic liquid medium" is meant a medium comprising at least one organic liquid, in other words at least one organic compound which is liquid at ambient temperature (25° C.) and atmospheric pressure ($10^5$ Pa). According to one mode of implementation, the majority liquid of the organic liquid medium is a volatile or non-volatile oil. Preferably, the organic liquid is cosmetically acceptable (acceptable tolerance, toxicology and feel). The organic liquid medium is cosmetically acceptable in the sense that it is compatible with keratin materials, such as the oils or organic solvents commonly employed in cosmetic compositions.

According to one mode of implementation, the majority liquid of the organic liquid medium is the polymerization solvent or one of the polymerization solvents of the block polymer, as are described below.

By polymerization solvent is meant a solvent or a mixture of solvents. The polymerization solvent may be selected in particular from ethyl acetate, butyl acetate, alcohols such as isopropanol and ethanol, aliphatic alkanes such as isododecane and isohexadecane, and mixtures thereof. Preferably the polymerization solvent is a mixture of butyl acetate and isopropanol, or isododecane or isohexadecane.

Preferentially, the (b) film-forming ethylenic polymer devoid of styrene does not include silicon atoms in its skeleton. By "skeleton" is meant the main chain of the polymer, as opposed to the pendant side chains.

Preferably, the (b) film-forming ethylenic polymer devoid of styrene is not water-soluble, which is to say that the polymer is not soluble in water or in a mixture of water and linear or branched lower monoalcohols having 2 to 5 carbon atoms, such as ethanol, isopropanol or n-propanol, without a change in pH, at an active substance content of at least 1% by weight, at ambient temperature (25° C.).

If the (b) film-forming linear ethylenic polymer is a block polymer, each block or sequence of the block polymer is obtained from one type of monomer or from two or more different types of monomers.

This signifies that each block may be composed of a homopolymer or of a copolymer; this copolymer, constituting the block, may in turn be random or alternating.

The glass transition temperatures indicated for the first and second blocks may be a theoretical Tg determined from the theoretical Tg of the constituent monomers of each of the blocks which can be found in a reference manual such as the Polymer Handbook, 3rd ed., 1989, John Wiley, according to the following relationship, called Fox's Law:

$$1/Tg = \Sigma_i (\omega_i/Tg_i)$$

with $\omega_i$ being the mass fraction of the monomer i in the block in question and $Tg_i$ being the glass transition temperature of the homopolymer of the monomer i.

Unless indicated otherwise, the Tg indicated for the first and second blocks in the present specification is a theoretical Tg.

The difference between the glass transition temperatures of the first and second blocks is generally greater than 10° C., preferably greater than 20° C., and more preferably greater than 30° C.

It is preferable that the block polymer comprise at least one first block and at least one second block such that the first block may be selected from:
i) a block with a Tg of greater than or equal to 40° C.,
ii) a block with a Tg of less than or equal to 20° C.,
iii) a block with a Tg of between 20 and 40° C.,
and the second block may be selected from category i), ii) or different from the first block.

In the present invention, the expression "between . . . and . . . " is intended to denote a range of values for which the limits mentioned are excluded, and the expression "from . . . to . . . " and "ranging from . . . to . . . " is intended to denote a range of values for which the limits are included.

i) Block with a Tg of Greater Than or Equal to 40° C.

The block with a Tg of greater than or equal to 40° C. may have, for example, a Tg ranging from 40 to 150° C., preferably greater than or equal to 50° C., ranging, for example, from 50° C. to 120° C., and better still greater than or equal to 60° C., ranging, for example, from 60° C. to 120° C.

The block with a Tg of greater than or equal to 40° C. may be a homopolymer or a copolymer.

The block with a Tg of greater than or equal to 40° C. may be obtained totally or partly from one or more monomers which are such that the homopolymer prepared from these monomers has a glass transition temperature of greater than or equal to 40° C.

In the case where this block is a homopolymer, it is obtained from monomers which are such that the homopolymers prepared from these monomers have glass transition temperatures of greater than or equal to 40° C. This first block may be a homopolymer composed of a single type of monomer (for which the Tg of the corresponding homopolymer is greater than or equal to 40° C.).

In the case where the first block is a copolymer, it may be obtained totally or partly from one or more monomers, the nature and concentration of which are selected such that the Tg of the resulting copolymer is greater than or equal to 40° C. The copolymer may comprise, for example: monomers which are such that the homopolymers prepared from these monomers have a Tg of greater than or equal to 40° C., for example, a Tg ranging from 40 to 150° C., preferably greater than or equal to 50° C., ranging, for example, from 50° C. to 120° C., and better still greater than or equal to 60° C., ranging, for example, from 60° C. to 120° C., and monomers which are such that the homopolymers prepared from these monomers have a Tg of less than 40° C., selected from monomers with a Tg of between 20 to 40° C. and/or monomers with a Tg of less than or equal to 20° C., for example a Tg ranging from −100 to 20° C., preferably less than 15° C., especially ranging from −80° C. to 15° C., and better still less than 10° C., for example ranging from −50° C. to 0° C., as described later.

The monomers whose homopolymers have a glass transition temperature of greater than or equal to 40° C. may be selected, preferably, from the following monomers, also known as principal monomers:

methacrylates of formula $CH_2=C(CH_3)-COOR_1$ in which $R_1$ represents a linear or branched unsubstituted alkyl group containing from 1 to 4 carbon atoms, such as a methyl, ethyl, propyl or isobutyl group, or $R_1$ represents a $C_4$ to $C_{12}$ cycloalkyl group;

acrylates of formula $CH_2=CH-COOR_2$ in which $R_2$ represents a $C_4$ to $C_{12}$ cycloalkyl group, such as isobornyl acrylate or a tert-butyl group;

(meth)acrylamides of formula:

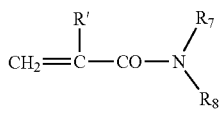

wherein $R_7$ and $R_8$, which are identical or different, each represent a hydrogen atom or a linear or branched $C_1$ to $C_{12}$ alkyl group, such as an n-butyl, t-butyl, isopropyl, isohexyl, isooctyl or isononyl group; or $R_7$ represents H and $R_8$ represents a 1,1-dimethyl-3-oxobutyl group and R' denotes H or methyl. Examples of monomers that may be mentioned include N-butylacrylamide, N-t-butylacrylamide, N-isopropylacrylamide, N,N-dimethylacrylamide and N,N-dibutylacrylamide; and mixtures thereof.

Principal monomers that are particularly preferred are methyl methacrylate, isobutyl methacrylate and isobornyl (meth)acrylate, and mixtures thereof.

Preferably, the proportion of the first block may range from 20% to 90% by weight, better still from 30% to 80% by weight, and even better still from 50% to 70% by weight of the polymer.

ii) Block with a Tg of Less Than or Equal to 20° C.

The block with a Tg of less than or equal to 20° C. has, for example, a Tg ranging from −100 to 20° C., preferably, less than or equal to 15° C., especially ranging from −80° C. to 15° C., and better still less than or equal to 10° C., for example ranging from −50° C. to 0° C.

The block with a Tg of less than or equal to 20° C. may be a homopolymer or a copolymer.

The block with a Tg of less than or equal to 20° C. may be obtained totally or partly from one or more monomers which are such that the homopolymer prepared from these monomers has a glass transition temperature of less than or equal to 20° C.

In the case where this block is a homopolymer, it is obtained from monomers which are such that the homopolymers prepared from these monomers have glass transition temperatures of less than or equal to 20° C. This second block may be a homopolymer composed of a single type of monomer (for which the Tg of the corresponding homopolymer is less than or equal to 20° C.).

In the case where the block with a Tg of less than or equal to 20° C. is a copolymer, it may be obtained totally or partly from one or more monomers, the nature and concentration of which are selected such that the Tg of the resulting copolymer is less than or equal to 20° C.

It may comprise, for example one or more monomers whose corresponding homopolymer has a Tg of less than or equal to 20° C., for example a Tg ranging from −100° C. to 20° C., preferably less than 15° C., especially ranging from −80° C. to 15° C., and better still less than 10° C., for example ranging from −50° C. to 0° C., and one or more monomers whose corresponding homopolymer has a Tg of greater than 20° C., such as monomers with a Tg of greater than or equal to 40° C., for example a Tg ranging from 40 to 150° C., preferably greater than or equal to 50° C., ranging for example from 50° C. to 120° C., and better still greater than or equal to 60° C., ranging for example from 60° C. to 120° C., and/or monomers with a Tg of between 20 and 40° C., as described above.

Preferably, the block with a Tg of less than or equal to 20° C. is a homopolymer.

The monomers whose homopolymer has a Tg of less than or equal to 20° C. may be selected, preferably, from the following monomers, or principal monomer:

acrylates of formula $CH_2=CHCOOR_3$, $R_3$ representing a linear or branched $C_1$ to $C_{12}$ unsubstituted alkyl group, with the exception of the tert-butyl group, in which one or more heteroatoms selected from O, N and S is (are) optionally intercalated;

methacrylates of formula $CH_2=C(CH_3)-COOR_4$, $R_4$ representing a linear or branched $C_6$ to $C_{12}$ unsubstituted alkyl group, in which one or more hetero-atoms selected from O, N and S is (are) optionally intercalated;

vinyl esters of formula $R_5-CO-O-CH-CH_2$ where $R_5$ represents a linear or branched $C_4$ to $C_{12}$ alkyl group;

$C_4$ to $C_{12}$ alkyl vinyl ethers;

N—($C_4$ to $C_{12}$ alkyl) acrylamides, such as N-octylacrylamide; and mixtures thereof.

The principal monomers that are particularly preferred for the block with a Tg of less than or equal to 20° C. are alkyl acrylates in which the alkyl chain contains from 1 to 10 carbon atoms, with the exception of the tert-butyl group, such as methyl acrylate, isobutyl acrylate and 2-ethylhexyl acrylate, and mixtures thereof.

Preferably, the proportion of the first block may range from 10% to 85% by weight, better still from 20% to 70% by weight, and even better still from 20% to 50% by weight of the polymer.

iii) Block with a Tg of between 20 and 40° C.

The (intermediate) block which has a Tg of between 20 and 40° C. may be a homopolymer or a copolymer.

The block with a Tg of between 20 and 40C° may be obtained totally or partly from one or more monomers which are such that the homopolymer prepared from these monomers has a glass transition temperature of between 20 and 40° C.

The block with a Tg of between 20 and 40° C. may be obtained totally or partly from monomers which are such that the corresponding homopolymer has a Tg of greater than or equal to 40° C. and from monomers which are such that the corresponding homopolymer has a Tg of less than or equal to 20° C.

In the case where this block is a homopolymer, it is obtained from monomers (or principal monomers) which are such that the homopolymers prepared from these monomers have glass transition temperatures of between 20 and 40° C. This intermediate block may be a homopolymer composed of a single type of monomer (for which the Tg of the corresponding homopolymer ranges from 20° C. to 40° C.).

The monomers whose homopolymer has a glass transition temperature of between 20 and 40° C. are selected, preferably, from n-butyl methacrylate, cyclodecyl acrylate, neopentyl acrylate and isodecylacrylamide, and mixtures thereof.

In the case where the block with a Tg of between 20 and 40° C. is a copolymer, it is obtained totally or partly from one or more monomers (or principal monomers) the nature and concentration of which are selected such that the Tg of the resulting copolymer is between 20 and 40° C.

Advantageously the block with a Tg of between 20 and 40° C. may be a copolymer obtained totally or partly from:

principal monomers whose corresponding homopolymer has a Tg of greater than or equal to 40° C., for example a Tg ranging from 40° C. to 150° C., preferably greater than or equal to 50° C., ranging for example from 50 to 120° C. and better still greater than or equal to 60° C., ranging for example from 60° C. to 120° C., as described above; and/or principal monomers whose corresponding homopolymer has a Tg of less than or equal to 20° C., for example a Tg ranging from −100 to 20° C., preferably less than or equal to 15° C., especially ranging from −80° C. to 15° C. and better still less than or equal to 10° C., for example ranging from −50° C. to 0° C., as described above, the said monomers being selected such that the Tg of the copolymer forming the first block is between 20 and 40° C.

Such principal monomers are selected, for example, from methyl methacrylate, isobornyl acrylate and methacrylate, butyl acrylate, isobutyl acrylate, 2-ethylhexyl acrylate, and mixtures thereof.

Preferably, each of the first and second blocks comprises at least one monomer selected from acrylic acid, the esters of acrylic acid, (meth)acrylic acid, the esters of (meth)acrylic acid, and mixtures thereof.

Advantageously, each of the first and second blocks is obtained totally from at least one monomer selected from acrylic acid, the esters of acrylic acid, (meth)acrylic acid, the esters of (meth)acrylic acid, and mixtures thereof.

However, each of the blocks may contain in minority proportion at least one constituent monomer of the other block.

Thus, the first block may contain at least one constituent monomer of the second block, and vice versa.

Each of the first and/or second blocks may comprise, in addition to the monomers indicated above, one or more other monomers known as additional monomers, which are different from the principal monomers mentioned above.

The nature and amount of this or these additional monomer(s) are selected such that the block in which they are present has the desired glass transition temperature.

This additional monomer is selected, for example, from:
a) hydrophilic monomers such as:
  ethylenically unsaturated monomers comprising at least one carboxylic or sulphonic acid function, for instance: acrylic acid, methacrylic acid, crotonic acid, maleic anhydride, itaconic acid, fumaric acid, maleic acid, acrylamidopropanesulphonic acid, vinylbenzoic acid, vinylphosphoric acid, and salts thereof;
  ethylenically unsaturated monomers comprising at least one tertiary amine function, for instance 2-vinylpyridine, 4-vinylpyridine, dimethylaminoethyl methacrylate, diethylaminoethyl methacrylate and dimethylaminopropylmethacrylamide, and salts thereof;
  methacrylates of formula $CH_2=C(CH_3)-COOR_6$ in which $R_6$ represents a linear or branched alkyl group containing from 1 to 4 carbon atoms, such as a methyl, ethyl, propyl or isobutyl group, the said alkyl group being substituted by one or more substituents selected from hydroxyl groups (for instance 2-hydroxypropyl methacrylate and 2-hydroxyethyl methacrylate) and halogen atoms (Cl, Br, I or F), such as trifluoroethyl methacrylate;
  methacrylates of formula $CH_2=C(CH_3)-COOR_9$, $R_9$ representing a linear or branched $C_6$ to $C_{12}$ alkyl group in which one or more heteroatoms selected from O, N and S is (are) optionally intercalated, the said alkyl group being substituted by one or more substituents selected from hydroxyl groups and halogen atoms (Cl, Br, I or F);
  acrylates of formula $CH_2=CHCOOR10$, $R_{10}$ representing a linear or branched $C_1$ to $C_{12}$ alkyl group substituted by one or more substituents selected from hydroxyl groups and halogen atoms (Cl, Br, I or F), such as 2-hydroxypropyl acrylate and 2-hydroxyethyl acrylate, or $R_{10}$ represents a $C_1$ to $C_{12}$ alkyl-O-POE (polyoxyethylene) with repetition of the oxyethylene unit from 5 to 30 times, for example methoxy-POE, or $R_{10}$ represents a polyoxyethylenated group comprising from 5 to 30 ethylene oxide units;
b) ethylenically unsaturated monomers comprising one or more silicon atoms, such as methacryloxypropyltrimethoxysilane and methacryloxypropyltris(trimethylsiloxy)silane; and mixtures thereof.

Additional monomers that are particularly preferred are acrylic acid, methacrylic acid and trifluoroethyl methacrylate, and mixtures thereof.

According to one embodiment, each of the first and second blocks of the block polymer comprises at least one monomer selected from esters of (meth)acrylic acid and optionally at least one additional monomer such as (meth)acrylic acid, and mixtures thereof.

According to another embodiment, each of the first and second blocks of the block polymer is obtained totally from at least one monomer selected from esters of (meth)acrylic acid and optionally at least one additional monomer such as (meth)acrylic acid, and mixtures thereof.

According to one preferred embodiment, the block polymer is a non-silicone polymer, i.e. a polymer free of silicon atoms.

This or these additional monomer(s) generally represent(s) an amount of less than or equal to 30% by weight, for example from 1% to 30% by weight, preferably from 5% to 20% by weight and more preferably from 7% to 15% by weight, relative to the total weight of the first and/or second blocks.

The block polymer may be obtained by free-radical solution polymerization according to the following preparation process:

a portion of the polymerization solvent is introduced into a suitable reactor and heated until the adequate temperature for the polymerization is reached (typically between 60 and 120° C.), once this temperature is reached, the constituent monomers of the first block are introduced in the presence of a portion of the polymerization initiator, after a time T corresponding to a maximum degree of conversion of 90%, the constituent monomers of the second block and the rest of the initiator are introduced, the mixture is left to react for a time T' (ranging from 3 to 6 hours), after which the mixture is cooled to ambient temperature, and the polymer in solution in the polymerization solvent is obtained.

(Specific Embodiments)

According to a first embodiment, the block polymer comprises a first block with a Tg of greater than or equal to 40° C., as described above in i), and a second block with a Tg of less than or equal to 20° C., as described above in ii).

Preferably, the first block with a Tg of greater than or equal to 40° C. is a copolymer obtained from monomers which are such that the homopolymer prepared from these monomers has a glass transition temperature of greater than or equal to 40° C., such as the monomers described above.

Advantageously, the second block with a Tg of less than or equal to 20° C. is a homopolymer obtained from monomers which are such that the homopolymer prepared from these monomers has a glass transition temperature of less than or equal to 20° C., such as the monomers described above.

Preferably, the proportion of the block with a Tg of greater than or equal to 40° C. may range from 20% to 90%, better still from 30% to 80% and even better still from 50% to 70% by weight of the polymer.

Preferably, the proportion of the block with a Tg of less than or equal to 20° C. ranges from 5% to 75%, preferably from 15% to 50% and better still from 25% to 45% by weight of the polymer.

Thus, according to a first variant, the (b) film-forming ethylenic polymer devoid of styrene may comprise:

a first block with a Tg of greater than or equal to 40° C., for example having a Tg ranging from 70 to 110° C., which is a methyl methacrylate/acrylic acid copolymer, a second block with a Tg of less than or equal to 20° C., for example ranging from 0 to 20° C., which is a methyl acrylate homopolymer, and an intermediate block which is a methyl methacrylate/acrylic acid/methyl acrylate copolymer.

According to a second variant, the (b) film-forming ethylenic polymer devoid of styrene may comprise:

a first block with a Tg of greater than or equal to 40° C., for example ranging from 70 to 100° C., which is a methyl methacrylate/acrylic acid/trifluoroethyl methacrylate copolymer, a second block with a Tg of less than or equal to 20° C., for example ranging from 0 to 20° C., which is a methyl acrylate homopolymer, and an intermediate block which is a methyl methacrylate/acrylic acid/methyl acrylate/trifluoro-ethyl methacrylate random copolymer.

According to a third variant, the (b) film-forming ethylenic polymer devoid of styrene may comprise:

a first block with a Tg of greater than or equal to 40° C., for example ranging from 85 to 115° C., which is an isobornyl acrylate/isobutyl methacrylate copolymer, a second block with a Tg of less than or equal to 20° C., for example ranging from −85 to −55° C., which is a 2-ethylhexyl acrylate homopolymer, and an intermediate block which is an isobornyl acrylate/isobutyl methacrylate/2-ethylhexyl acrylate random copolymer.

According to a fourth variant, the (b) film-forming ethylenic polymer devoid of styrene may comprise: a first block with a Tg of greater than or equal to 40° C., for example ranging from 85 to 115° C., which is an isobornyl acrylate/methyl methacrylate copolymer, a second block with a Tg of less than or equal to 20° C., for example ranging from −85 to −55° C., which is a 2-ethylhexyl acrylate homopolymer, and an intermediate block which is an isobornyl acrylate/methyl methacrylate/2-ethylhexyl acrylate random copolymer.

According to a fifth variant, the (b) film-forming ethylenic polymer devoid of styrene may comprise: a first block with a Tg of greater than or equal to 40° C., for example ranging from 95 to 125° C., which is an isobornyl acrylate/isobornyl methacrylate copolymer, a second block with a Tg of less than or equal to 20° C., for example ranging from −85 to −55° C., which is a 2-ethylhexyl acrylate homopolymer, and an intermediate block which is an isobornyl acrylate/isobornyl methacrylate/2-ethylhexyl acrylate random copolymer.

According to a sixth variant, the (b) film-forming ethylenic polymer devoid of styrene may comprise: a first block with a Tg of greater than or equal to 40° C., for example ranging from 85 to 115° C., which is an isobornyl methacrylate/isobutyl methacrylate copolymer, a second block with a Tg of less than or equal to 20° C., for example ranging from −35 to −5° C., which is an isobutyl acrylate homopolymer, and an intermediate block which is an isobornyl methacrylate/isobutyl methacrylate/isobutyl acrylate random copolymer.

According to a seventh variant, the (b) film-forming ethylenic polymer devoid of styrene may comprise:

a first block with a Tg of greater than or equal to 40° C., for example ranging from 95 to 125° C., which is an isobornyl acrylate/isobornyl methacrylate copolymer, a second block with a Tg of less than or equal to 20° C., for example ranging from −35 to −5° C., which is an isobutyl acrylate homopolymer, and an intermediate block which is an isobornyl acrylate/isobornyl methacrylate/isobutyl acrylate random copolymer.

According to an eighth variant, the (b) film-forming ethylenic polymer devoid of styrene may comprise:

a first block with a Tg of greater than or equal to 40° C., for example ranging from 60 to 90° C., which is an isobornyl acrylate/isobutyl methacrylate copolymer, a second block with a Tg of less than or equal to 20° C., for example ranging from −35 to −5° C., which is an isobutyl acrylate homopolymer, and an intermediate block which is an isobornyl acrylate/isobutyl methacrylate/isobutyl acrylate random copolymer.

According to a ninth variant, the (b) film-forming ethylenic polymer devoid of styrene may comprise:

a first block with a Tg of greater than or equal to 40° C., for example ranging from 100 to 200° C., which is an isobornyl acrylate homopolymer, a second block with a Tg of less than or equal to 20° C., for example ranging from −30 to −10° C., which is an isobutyl acrylate and acrylic acid copolymer, and an intermediate block which is an isobornyl acrylate/acrylic acid/isobutyl acrylate random copolymer.

It is preferable that the (b) film-forming linear ethylenic polymer devoid of styrene be acrylic acid/isobutyl acrylate/isobornyl acrylate copolymer, for example, Mexomere PAS.

The (b) film-forming ethylenic polymer devoid of styrene may be present in the composition in a content ranging from 0.01% to 10% by weight, preferably ranging from 0.05 to 5% by weight, and more preferably from 0.1 to 2% by weight, relative to the total weight of the composition.

[Oil]

The composition according to the present invention comprises at least one (c) oil. If two or more (c) oils are used, they may be the same or different.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The oil may be a non-polar oil such as a hydrocarbon oil, a silicone oil, or the like; a polar oil such as a plant or animal oil and an ester oil or an ether oil; or a mixture thereof.

The oil may be selected from the group consisting of oils of plant or animal origin, synthetic oils, silicone oils, hydrocarbon oils and fatty alcohols.

As examples of plant oils, mention may be made of, for example, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols, and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used according to the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:
(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:

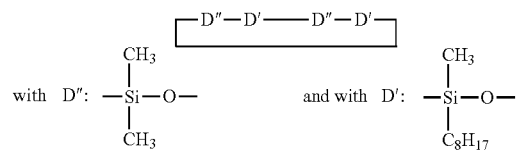

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2', 2',3,3'-hexatrimethylsilyloxy)neopentane; and (ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, Jan. 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s; and the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250 and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

$$R_9-\underset{\underset{R_2}{|}}{\overset{\overset{R_1}{|}}{Si}}-O-\left[\underset{\underset{R_4}{|}}{\overset{\overset{R_3}{|}}{Si}}-O\right]_p-\left[\underset{}{\overset{\overset{Ph}{|}}{Si}}-O\right]_q-\left[\underset{\underset{R_8}{|}}{\overset{\overset{Ph}{|}}{Si}}-O\right]_q-\left[\underset{\underset{Ph}{|}}{\overset{\overset{Ph}{|}}{Si}}-O\right]_n-\underset{\underset{O}{|}\ Si-(R_{10})_3}{\overset{\overset{R_5}{|}}{Si}}-O-\underset{\underset{R_7}{|}}{\overset{\overset{R_5}{|}}{Si}}-R_6$$

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl or butyl radicals, and m, n, p and q are, independently of each other, integers 0 to 900 inclusive, preferably 0 to 500 inclusive, and more preferably 0 to 100 inclusive, with the proviso that the sum n+m+q is other than 0.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty, alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from octyldodecanol, hexyldecanol and mixtures thereof.

It is preferable that the (a) oil be chosen from hydrocarbon oils, more preferably volatile hydrocarbon oils, and even more preferably volatile branched hydrocarbons oils, such as isododecane and isohexadecane.

The amount of the (a) oil in the composition according to the present invention may range from 0.1 to 20% by weight, preferably from 0.5 to 15% by weight, and more preferably from 1 to 10% by weight, relative to the total weight of the composition.

Since the composition according to the present invention comprises at least one (a) oil, the composition according to the present invention also comprises at least one fatty phase.

Since the composition according to the present invention is in the form of an O/W emulsion, the fatty phase in the composition according to the present invention can be the dispersed as inner phases in the O/W emulsion.

The amount of the fatty phase in the composition according to the present invention is 30% by weight or less, preferably 25% by weight or less, more preferably 20% by weight or less, and even more preferably 15% by weight or less, relative to the total weight of the composition.

On the other hand, the amount of the fatty phase in the composition according to the present invention may be 0.1% by weight or more, preferably 0.5% by weight or more, and more preferably 1% by weight or more, relative to the total weight of the composition.

Thus, for example, the amount of the fatty phase may be from 0.1 to 30% by weight, preferably from 0.1% to 25% by weight, more preferably from 0.5% to 20% by weight, and even more preferably from 1.5% to 15% by weight, in relation to the total weight of the composition.

[Water]

The composition according to the present invention comprises (d) water.

The amount of the (d) water may be from 40 to 90% by weight, preferably from 50 to 80% by weight, and more preferably from 60 to 70% by weight, relative to the total weight of the composition.

Since the composition according to the present invention comprises (d) water, the composition according to the present invention also comprises an aqueous phase as a continuous outer phase of the composition in the form of an O/W emulsion.

The aqueous phase may comprise at least one $C_2$-$C_6$ monohydric alcohol. Two or more $C_2$-$C_6$ monohydric alcohols may be used in combination.

The $C_2$-$C_6$ monohydric alcohol suitable for the present invention may comprise from 2 to 5 carbon atoms, preferably from 2 to 4 carbon atoms, such as ethanol, isopropanol, propanol or butanol.

Ethanol and isopropanol, and preferably ethanol, are very particularly suitable for the present invention.

The amount of the $C_2$-$C_6$ monohydric alcohol in the composition according to the present invention may be 20% by weight or less, preferably 15% by weight or less, and more preferably 10% by weight or less, relative to the total weight of the composition. On the other hand, the amount of the $C_2$-$C_6$ monohydric alcohol in the composition according to the present invention is 5% by weight or more, preferably 6% by weight or more, and more preferably 7% by weight or more, relative to the total weight of the composition. For example, the amount of the $C_2$-$C_6$ monohydric alcohol may be from 5% to 20% by weight, preferably from 6% to 15% by weight, and more preferably from 7% to 10% by weight, in relation to the total weight of the composition.

The aqueous phase may comprise polyhydric alcohols containing 1 to 8 carbon atoms such as propylene glycol, ethylene glycol, 1,3-butylene glycol, dipropylene glycol, diethylene glycol, hexyleneglycol, glycerin, and mixtures thereof.

The amount of the polyhydric alcohol(s) such as glycols, if present, in the aqueous phase according to the present invention may range from 0.1 to 15% by weight, preferably from 0.5 to 12% by weight, and more preferably from 1 to 8% by weight, relative to the total weight of the composition.

[Hydrophilic Thickener]

The composition according to the present invention may include at least one (e) hydrophilic thickener. If two or more hydrophilic thickeners are used, they may be the same or different.

The (e) hydrophilic thickener can thicken the aqueous phase of the composition according to the present invention.

It is preferable that the (e) hydrophilic thickener be a synthetic hydrophilic thickener.

It is more preferable that the (e) hydrophilic thickener be a non-crosslinked synthetic hydrophilic thickener.

Hydrophilic thickeners that may be mentioned include carboxyvinyl polymers such as the Carbopol products (carbomers) and the Pemulen products (acrylate/C10-C30-alkyl acrylate copolymer); polyacrylamides, for instance those sold under the names Sepigel 305 (CTFA name: polyacrylamide/C13-C14 isoparaffin/Laureth 7) sold by the company SEPPIC; acryloyldimethyl taurate copolymers, for instance, Simulgel FL (CTFA name: hydroxyethylacrylate/sodium acryloyldimethyl taurate copolymer/polysorbate 60), Simulgel 800 (CTFA name: sodium polyacryloyldimethyl taurate/polysorbate 80/sorbitan oleate) or Simulgel 600 (CTFA name: acrylamide/sodium acryloyldimethyl taurate copolymer/isohexadecane/polysorbate 80) sold by the company SEPPIC; 2-acrylamido-2-methylpropanesulfonic acid polymers and copolymers, optionally neutralized, for instance poly(2-acrylamido-2-methylpropanesulfonic acid) sold by the company Clariant under the trade name Hostacerin AMPS (CTFA name: ammonium polyacryloyldimethyl taurate) copolymers of 2-acrylamido-2-methylpropanesulfonic acid and of hydroxyethyl acrylate, for instance Simulgel NS and Sepinov EMT 10 sold by the company SEPPIC; celluloses derivatives such as hydroxyethyl cellulose and mixtures thereof. Acryloyldimethyl taurate copolymers, such as Simulgel FL, Simulgel 800 and Simulgel 600, are preferable in terms of bulk feasibility, adhesiveness on skin and lasting effect.

The (e) hydrophilic thickener may be present in the composition in a content ranging from 0.01% to 15% by weight, preferably ranging from 0.1% to 10% by weight, and more preferably from 0.5 to 5% by weight, relative to the total weight of the composition.

[Associative Polymer]

The composition according to the present invention may include at least one (f) associative polymer. If two or more associative polymers are used, they may be the same or different.

As used herein, the expression "associative polymer" means an amphiphilic polymer comprising both hydrophilic units and hydrophobic units, for example, at least one $C_8$-$C_{30}$ fatty chain and at least one hydrophilic unit.

Representative associative polymers that may be used are those chosen from:
(1) nonionic amphiphilic polymers comprising at least one fatty chain and at least one hydrophilic unit;
(2) anionic amphiphilic polymers comprising at least one hydrophilic unit and at least one fatty-chain unit;
(3) cationic amphiphilic polymers comprising at least one hydrophilic unit and at least one fatty-chain unit; and
(4) amphoteric amphiphilic polymers comprising at least one hydrophilic unit and at least one fatty-chain unit,
wherein the fatty chain unit contains from 10 to 30 carbon atoms.

The (1) nonionic amphiphilic polymers comprising at least one fatty chain unit and at least one hydrophilic unit may, for example, be chosen from:
(i) celluloses modified with groups comprising at least one fatty chain; examples that may be mentioned include:
hydroxyethylcelluloses modified with groups comprising at least one fatty chain chosen from alkyl, arylalkyl and alkylaryl groups, and in which the alkyl groups are, for example, $C_8$-$C_{22}$, such as the product Natrosol Plus Grade 330 CS($C_1$-$C_6$ alkyls) sold by the company Aqualon, and the product Bermocoll EHM 100 sold by the company Berol Nobel, and
celluloses modified with polyalkylene glycol alkylphenyl ether groups, such as the product Amercell Polymer HM-1500 (polyethylene glycol (15) nonylphenyl ether) sold by the company Amerchol;
(ii) hydroxypropyl guars modified with groups comprising at least one fatty chain, such as the product Esaflor HM 22 ($C_{22}$ alkyl chain) sold by the company Lamberti, and the products Miracare XC95-3 ($C_{14}$ alkyl chain) and RE205-1 ($C_{20}$ alkyl chain) sold by the company Rhodia Chimie;
(iii) polyether urethanes comprising at least one fatty chain, such as $C_{10}$-$C_{30}$ alkyl or alkenyl groups, for instance the products Elfacos T 210 and Elfacos T 212 sold by the company Akzo or the products Aculyn 44 and Aculyn 46 sold by the company Rohm & Haas;
(iv) copolymers of vinylpyrrolidone and of hydrophobic fatty-chain monomers; examples that may be mentioned include:

the products Antaron V216 and Ganex V216 (vinylpyrrolidone/hexadecene copolymer) sold by the company I.S.P., and
the products Antaron V220 and Ganex V220 (vinylpyrrolidone/eicosene copolymer) sold by the company I.S.P.;
(v) copolymers of $C_1$-$C_6$ alkyl acrylates or methacrylates and of amphiphilic monomers comprising at least one fatty chain, such as the oxyethylenated methyl methacrylate/stearyl acrylate copolymer sold by the company Goldschmidt under the name Antil 208;
(vi) copolymers of hydrophilic acrylates or methacrylates and of hydrophobic monomers comprising at least one fatty chain, such as polyethylene glycol methacrylate/lauryl methacrylate copolymer.

The (2) anionic amphiphilic polymers comprising at least one hydrophilic unit and at least one fatty-chain unit, may, for example, be chosen from those comprising at least one fatty-chain allyl ether unit and at least one hydrophilic unit comprising an ethylenic unsaturated anionic monomeric unit, for example, a vinylcarboxylic acid unit and further, for example, be chosen from units derived from acrylic acids, methacrylic acids and mixtures thereof, wherein the fatty-chain allyl ether unit corresponds to the monomer of formula (I) below:

$$CH_2=C(R_1)CH_2OB_nR \qquad (I)$$

in which $R_1$ is chosen from H and $CH_3$, B is an ethyleneoxy radical, n is chosen from zero and integers ranging from 1 to 100, R is chosen from hydrocarbon-based radicals chosen from alkyl, arylalkyl, aryl, alkylaryl and cycloalkyl radicals, containing from 10 to 30 carbon atoms, and further, for example, from 10 to 24 carbon atoms and even further, for example, from 12 to 18 carbon atoms.

In one embodiment, a unit of formula (I) is, for example, a unit in which $R_1$ can be H, n can be equal to 10, and R can be a stearyl ($C_{18}$) radical.

Anionic amphiphilic polymers of this type are described and prepared, according to an emulsion polymerization process, in patent EP-0 216 479 B2.

In one embodiment, anionic amphiphilic polymers are, for example, polymers formed from 20% to 60% by weight of acrylic acid and/or of methacrylic acid, from 5% to 60% by weight of lower alkyl (meth)acrylates, from 2% to 50% by weight of fatty-chain ally! ether of formula (I), and from 0% to 1% by weight of a crosslinking agent which is a well-known copolymerizable unsaturated polyethylenic monomer, for example, diallyl phthalate, allyl(meth)acrylate, divinylbenzene, (poly)ethylene glycol dimethacrylate and methylenebisacrylamide.

Examples of such polymers are crosslinked terpolymers of methacrylic acid, of ethyl acrylate and of polyethylene glycol (10 EO) stearyl ether (Steareth-10), such as those sold by the company Ciba under the names Salcare SC 80 and Salcare SC 90, which are aqueous 30% emulsions of a crosslinked terpolymer of methacrylic acid, of ethyl acrylate and of steareth-10 allyl ether (40/50/10).

The anionic amphiphilic polymers may further be chosen, for example, from those comprising at least one hydrophilic unit of unsaturated olefinic carboxylic acid type, and at least one hydrophobic unit of a type such as a ($C_{10}$-$C_{30}$) alkyl ester of an unsaturated carboxylic acid. The hydrophilic unit of unsaturated olefinic carboxylic acid type corresponds to, for example, the monomer of formula (II) below:

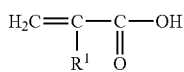

in which $R^1$ is chosen from H, $CH_3$ and $C_2H_5$, i.e. acrylic acid, methacrylic acid and ethacrylic acid units. The hydrophobic unit of a type such as a ($C_{10}$-$C_{30}$) alkyl ester of an unsaturated carboxylic acid corresponds to, for example, the monomer of formula (III) below:

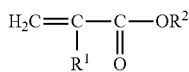

in which $R^1$ is chosen from H, $CH_3$ and $C_2H_5$ (i.e. acrylate, methacrylate and ethacrylate units) and is, for example, chosen from H (acrylate units) and $CH_3$ (methacrylate units), $R^2$ is chosen from $C_{10}$-$C_{30}$ alkyl radicals, for example, $C_{12}$-$C_{22}$ alkyl radicals.

Examples of ($C_{10}$-$C_{30}$) alkyl esters of unsaturated carboxylic acids include lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are disclosed and prepared, for example, according to U.S. Pat. Nos. 3,915,921 and 4,509,949.

Representative anionic amphiphilic polymers that can be used may further be chosen from polymers formed from a mixture of monomers comprising:
(vii) acrylic acid, an ester of formula (IV) below:

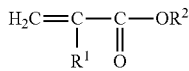

in which $R^1$ is chosen from H and $CH_3$, $R^2$ is chosen from $C_{10}$-$C_{30}$ alkyl radicals, such as alkyl radicals containing from 12 to 22 carbon atoms, and a crosslinking agent; such as polymers derived from 95% to 60% by weight of the acrylic acid (hydrophilic unit), 4% to 40% by weight of $C_{10}$-$C_{30}$ alkyl acrylate (hydrophobic unit), and 0% to 6% by weight of crosslinking polymerizable monomer, or polymers derived from 98% to 96% by weight of the acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer; or
(viii) acrylic acid and lauryl methacrylate, such as the polymers formed from 66% by weight of acrylic acid and 34% by weight of lauryl methacrylate.

The crosslinking agent can be a monomer comprising a group

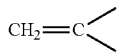

with at least one other polymerizable group whose unsaturated bonds are not conjugated.

Mention may be made, for example, of polyallyl ethers such as polyallylsucrose and polyallylpentaerythritol.

Among said polymers above, mention may be made, for example, of the products sold by the company Goodrich under the trade names Pemulen TR1, Pemulen TR2, Carbopol 1382, and further, for example, Pemulen TR1, and the product sold by the company S.E.P.C. under the name Coatex SX.

Among anionic amphiphilic fatty-chain polymers, mention may also be made, for example, of the ethoxylated copolymer of methacrylic acid/methyl acrylate/alkyl dimethyl-meta-isopropenylbenzylisocyanate sold under the name Viscophobe DB 1000 by the company Amerchol.

The (3) cationic amphiphilic polymers used are, for example, chosen from quatemized cellulose derivatives and polyacrylates comprising amino side groups.

The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, and quaternized hydroxyethylcelluloses modified with groups comprising at least one fatty chain, such as alkyl, arylalkyl and alkylaryl groups comprising at least 8 carbon atoms, and mixtures thereof.

Quatemized and non-quaternized polyacrylates comprising amino side groups have, for example, hydrophobic groups, such as Steareth 20 (polyoxy-ethylenated (20) stearyl alcohol) and ($C_{10}$-$C_{30}$)alkyl PEG-20 itaconate.

The alkyl radicals borne by the above quaternized celluloses and hydroxyethylcelluloses, for example, contain from 8 to 30 carbon atoms.

The aryl radicals, for example, are chosen from phenyl, benzyl, naphthyl and anthryl groups.

Examples of quaternized alkylhydroxyethyl-celluloses comprising $C_8$-$C_{30}$ fatty chains are the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol, and the products Crodacel QM, Crodacel QL ($C_{12}$ alkyl) and Crodacel QS ($C_{18}$ alkyl) sold by the company Croda.

Examples of polyacrylates comprising amino side chains are the polymers 8781-124B or 9492-103 and Structure Plus from the company National Starch.

Among (4) amphoteric amphiphilic polymers comprising at least one hydrophilic unit and at least one fatty-chain unit, mention may be made, for example, of copolymers of methacrylamidopropyltrimethylammonium chloride/acrylic acid/$C_{10}$-$C_{30}$ alkyl methacrylate, wherein the alkyl radical is, for example, a stearyl radical.

The associative polymers can have, for example, in solution or in dispersion at a concentration of 1% active material in water, a viscosity, measured using a Rheomat RM 180 rheometer at 25° C., of greater than 0.1 ps and further, for example, of greater than 0.2 cp, at a shear rate of 200 $s^{-1}$.

The (a) associative polymer may be an associative polyurethane polymer.

The associative polyurethane polymer may be cationic or nonionic.

Among the associative polyurethane polymers, there may be mentioned the associative polyurethane derivatives such as those obtained by polymerization: about 20% to 70% by weight of a carboxylic acid containing an α,β-monoethylenic unsaturation, about 20 to 80% by weight of a nonsurfactant monomer containing an α,β-monoethylenic unsaturation, about 0.5 to 60% by weight of a nonionic monourethane which is the product of the reaction of a monohydroxylated surfactant with a monoethylenically unsaturated monoisocyanate.

The like are described in particular in EP 173109 and more particularly in example 3. More precisely, this polymer is a methacrylic acid/methyl acrylate/dimethyl metaisopropenyl benzyl isocyanate of ethoxylated behenyl alcohol (40EO) terpolymer as an aqueous dispersion at 25%. This product is provided under the reference VISCOPHOBE DB1000 by the company AMERCHOL.

Also suitable are the cationic associative polyurethane polymers the family of which has been described by the Applicant in French Patent Application No. 0009609. It can be represented more particularly by the following general formula (A): $RX-(P)_n-[L-(Y)_m]_r-L'-(P')_p-X'-R'$ (A) in which: R and R', which are identical or different, represent a hydrophobic group or a hydrogen atom; X and X', which are identical or different, represent a group containing an amine functional group carrying or otherwise a hydrophobic group, or alternatively the group L''; L, L' and L'', which are identical or different, represent a group derived from a diisocyanate; P and P', which are identical or different, represent a group containing an amine functional group carrying or otherwise a hydrophobic group; Y represents a hydrophilic group; r is an integer between 1 and 100, preferably between 1 and 50 and in particular between 1 and 25; n, m and p are each independently of the others between 0 and 1000; the molecule containing at least one protonated or quaternized amine functional group and at least one hydrophobic group.

In a very advantageous embodiment, the only hydrophobic groups of these polyurethanes are the groups R and R' at the chain ends.

According to a first preferred embodiment, the associative polyurethane polymer corresponds to the formula (A) in which R and R' both represent independently a hydrophobic group; X and X' each represent a group L''; n and p are between 1 and 1000; and L, L', L'', P, P', Y and m have the meanings indicated in formula (A).

According to another preferred embodiment of the present invention, the associative polyurethane polymer corresponds to the formula (A) in which R and R' both represent independently a hydrophobic group; X and X' each represent a group L''; n and p are equal to 0; and L, L', L'', Y and m have the meanings in formula (A) indicated above.

The fact that n and p are equal to 0 means that these polymers do not contain units derived from a monomer containing an amine functional group, incorporated into the polymer during polycondensation. The protonated amine functional groups of these polyurethanes result from the hydrolysis of isocyanate functional groups, in excess, at the chain end, followed by alkylation of the primary amine functional groups formed by alkylating agents containing a hydrophobic group, that is to say compounds of the RQ or R'Q type, in which R and R' are as defined above and Q denotes a leaving group such as a halide, a sulfate and the like.

In accordance with another preferred embodiment of the present invention, the associative polyurethane polymer corresponds to formula (A) in which R and R both represent independently a hydrophobic group; X and X' both represent independently a group containing a quaternary amine; n and p are equal to zero; and L, L', Y and m have the meaning indicated in formula (A).

The number-average molecular mass of the cationic associative polyurethane polymers is usually between 400 and 500 000, in particular between 1000 and 400 000, and ideally between 1000 and 300 000 g/mol.

When X and/or X' denote a group containing a tertiary or quaternary amine, X and/or X' may represent one of the following formulae:

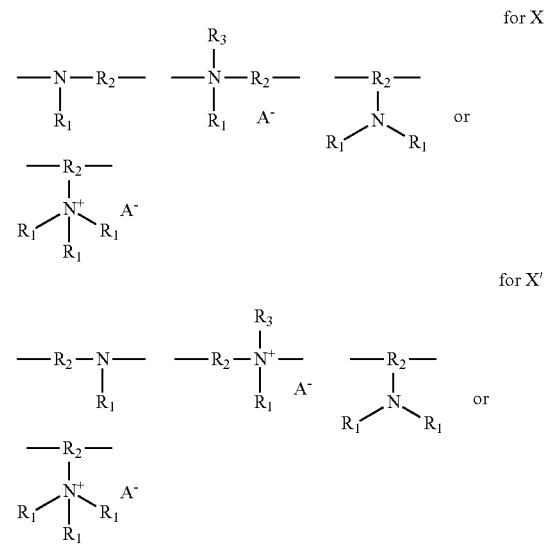

in which:

$R_2$ represents a linear or branched alkylene radical having from 1 to 20 carbon atoms, containing or otherwise a saturated or unsaturated ring, or an arylene radical, it being possible for one or more of the carbon atoms to be replaced by a heteroatom chosen from N, S, O, P;

$R_1$ and $R_3$, which are identical or different, denote a linear or branched, $C_1$-$C_{30}$ alkyl or alkenyl radical, an aryl radical, it being possible for at least one of the carbon atoms to be replaced by a heteroatom chosen from N, S, O, and P;

$A^-$ is a physiologically acceptable counterion.

The groups L, L' and L'' represent a group of formula:

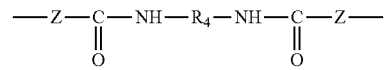

in which:

Z represents —O—, —S— or —NH—; and $R_4$ represents a linear or branched alkylene radical having from 1 to 20 carbon atoms, containing or otherwise a saturated or unsaturated ring, an arylene radical, it being possible for one or more of the carbon atoms to be replaced by a heteroatom chosen from N, S, O and P.

The groups P and P', comprising an amine functional group, may represent at least one of the following formulae:

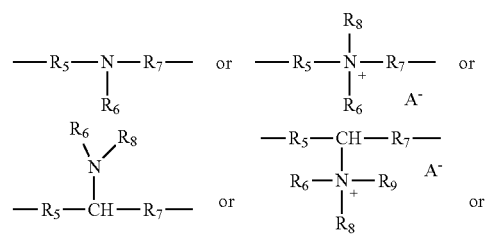

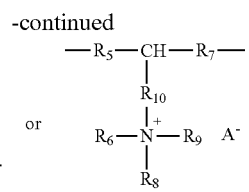

in which:

$R_5$ and $R_7$ have the same meanings as $R_2$ defined above;
$R_6$, $R_8$ and $R_9$ have the same meanings as $R_1$ and $R_3$ defined above;

$R_{10}$ represents a linear or branched alkylene group, which is optionally unsaturated and which may contain one or more heteroatoms chosen from N, O, S and P;

$A^-$ is a physiologically acceptable counterion.

As regards the meaning of Y, the expression hydrophilic group is understood to mean a polymeric or nonpolymeric water-soluble group. By way of example, there may be mentioned, when polymers are not involved, ethylene glycol, diethylene glycol and propylene glycol. In accordance with a preferred embodiment, in the case of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The cationic associative polyurethane polymers of formula (A) are formed from diisocyanates and from various compounds possessing functional groups containing a labile hydrogen. The functional groups containing a labile hydrogen may be alcohol functional groups, primary or secondary amine functional groups or thiol functional groups which give, after reaction with the diisocyanate functional groups, polyurethanes, polyureas and polythioureas, respectively. The term "polyurethanes" of the present invention covers these three types of polymer, namely polyurethanes proper, polyureas and polythioureas and copolymers thereof.

A first type of compounds entering into the preparation of the polyurethane of formula (A) is a compound containing at least one unit containing an amine functional group. This compound may be multifunctional, but preferably the compound is difunctional, that is to say, according to a preferred embodiment, this compound contains two labile hydrogen atoms carried for example by a hydroxyl, primary amine, secondary amine or thiol functional group. It is also possible to use a mixture of multifunctional and difunctional compounds in which the percentage of multifunctional compounds is low.

As indicated above, this compound may contain more than one unit containing an amine functional group. It is then a polymer carrying a repeat of the unit containing an amine functional group.

This type of compound may be represented by one of the following formulae: $HZ\text{-}(P)_n\text{-}ZH$, or $HZ\text{-}(P')^p\text{-}ZH$, in which Z, P, P', n and p are as defined above.

By way of examples of a compound containing an amine functional group, there may be mentioned N-methyldiethanolamine, N-tert-butyldiethanolamine, N-sulfoethyldiethanolamine.

The second compound entering into the preparation of the polyurethane of formula (A) is a diisocyanate corresponding to the formula $O=C=N-R_4-N=C=O$ in which $R_4$ is defined above.

By way of example, there may be mentioned methylenediphenyl diisocyanate, methylenecyclohexane diisocyanate, isophorone diisocyanate, toluene diisocyanate, naphthalene diisocyanate, butane diisocyanate, and hexane diisocyanate.

A third compound entering into the preparation of the polyurethane of formula (A) is a hydrophobic compound intended to form the terminal hydrophobic groups of the polymer of formula (A).

This compound consists of a hydrophobic group and a functional group containing a labile hydrogen, for example a hydroxyl, primary or secondary amine, or thiol functional group.

By way of example, this compound may be a fatty alcohol, such as in particular stearyl alcohol, dodecyl alcohol, and decyl alcohol. When this compound contains a polymeric chain, it may be for example a hydroxyl hydrogenated polybutadiene.

The hydrophobic group of the polyurethane of formula (A) may also result from the quaternization reaction of the tertiary amine of the compound containing at least one tertiary amine unit. Thus, the hydrophobic group is introduced by the quaternizing agent. This quaternizing agent is a compound of the RQ or R'Q type, in which R and R' are as defined above and Q denotes a leaving group such as a halide, and a sulfate.

The cationic associative polyurethane polymer may additionally comprise a hydrophilic sequence. This sequence is provided by a fourth type of compound entering into the preparation of the polymer. This compound may be multifunctional. It is preferably difunctional. It is also possible to have a mixture where the percentage of multifunctional compound is low.

The functional groups containing a labile hydrogen are alcohol, primary or secondary amine, or thiol functional groups. This compound may be a polymer terminated at the chain ends by one of these functional groups containing a labile hydrogen.

By way of example, there may be mentioned, when polymers are not involved, ethylene glycol, diethylene glycol and propylene glycol.

In the case of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The hydrophilic group noted Y in formula (A) is optional. Indeed, the units containing a quaternary or protonated amine functional group may suffice to provide the solubility or water-dispersibility necessary for this type of polymer in an aqueous solution. Although the presence of a hydrophilic group Y is optional, cationic associative polyurethane polymers are nevertheless preferred which contain such a group.

The associative polyurethane polymer used in the present invention may also be nonionic, in particular nonionic polyurethane-polyethers. The nonionic polyurethane-polyethers may have both at least one hydrophilic moiety and at least one hydrophobic moiety. More particularly, said polymers may contain in their chain both hydrophilic sequences most often of a polyoxyethylenated nature and hydrophobic sequences which may be aliphatic linkages alone and/or cycloaliphatic and/or aromatic linkages.

Preferably, these polyether-polyurethanes comprise at least two lipophilic hydrocarbon chains, having from 6 to 30 carbon atoms, preferably from 6 to 20, separated by a hydrophilic sequence, and it being possible for the hydrocarbon chains to be pendent chains or chains at the end of a hydrophilic sequence. In particular, it is possible for one or more pendent chains to be envisaged. In addition, the polymer may comprise a hydrocarbon chain at one end or at both ends of a hydrophilic sequence.

The polyether-polyurethanes may be polyblocks, in particular in triblock form. The hydrophobic sequences may be at each end of the chain (for example: triblock copolymer with hydrophilic central sequence) or distributed both at the ends and in the chain (polyblock copolymers for example). These same polymers may also be in the form of graft units or may be star-shaped.

The associative polyurethane polymer can form a network in water in which the hydrophobic part connects quasi-micelles as shown in FIG. 1.

Therefore, the associative polyurethane polymers can increase viscosity or consistency of the composition according to the present invention. Thus, after application of the composition according to the present invention, it can recover the original elasticity of the composition quickly.

The nonionic polyether-polyurethanes containing a fatty chain may be triblock copolymers whose hydrophilic sequence is a polyoxyethylenated chain comprising from 50 to 1000 oxyethylenated groups.

The nonionic polyether-polyurethanes comprise a urethane bond between the hydrophilic sequences, hence the origin of the name.

By extension, those whose hydrophilic sequences are linked by other chemical bonds to the hydrophobic sequences are also included among the nonionic polyether-polyurethanes containing a hydrophobic chain.

By way of examples of nonionic polyether-polyurethanes containing a hydrophobic chain which can be used in the present invention, it is also possible to use Rheolate® 205 containing a urea functional group sold by the company RHEOX or else the Rheolates® 208, 204 or 212, as well as Acrysol RM 184®.

There may also be mentioned the product ELFACOS T210® containing a $C_{12}$-$C_{14}$ alkyl chain and the product ELFACOS T212® containing a $C_{18}$ alkyl chain from AKZO.

The product DW 1206B® from ROHM & HAAS containing a $C_{20}$ alkyl chain and with a urethane bond, sold at 20% dry matter content in water, may also be used.

It is also possible to use solutions or dispersions of these polymers in particular in water or in an aqueous-alcoholic medium. By way of examples of such polymers, there may be mentioned Rheolate® 255, Rheolate® 278 and Rheolate® 244 sold by the company RHEOX. It is also possible to use the product DW 1206F and DW 1206J provided by the company ROHM & HAAS.

The above-described polyether-polyurethanes which can be used can also be chosen from those described in the article by G. Fonnum, J. Bakke and Fk. Hansen-Colloid Polym. Sci 271, 380-389 (1993).

As the above-described polyether-polyurethanes, mention may be made of polyurethane-polyethers comprising in their chain at least one polyoxyethylenated hydrophilic block and at least one of hydrophobic blocks containing at least one sequence chosen from aliphatic sequences, cycloaliphatic sequences, and aromatic sequences.

It may be preferable that the polyurethane-polyethers comprise at least two hydrocarbon-based lipophilic chains having from 8 to 30 carbon atoms, separated by a hydrophilic block, and wherein the hydrocarbon-based chains are chosen from pendent chains and chains at the end of the hydrophilic block.

According to a specific form of the present invention, use will be made of a polyurethane/polyether that may be obtained by polycondensation of at least three compounds comprising (i) at least one polyethylene glycol comprising from 150 to 180 mol of ethylene oxide, (ii) a polyoxyethylenated stearyl alcohol comprising 100 mol of ethylene oxide, and (iii) a diisocyanate.

Such polyurethane/polyethers are sold especially by the company Elementis under the name Rheolate FX 1100® and Rheoluxe 811®, which is a polycondensate of polyethylene glycol containing 136 mol of ethylene oxide, of stearyl alcohol polyoxyethylenated with 100 mol of ethylene oxide and of hexamethylene diisocyanate (HDI) with a weight-average molecular weight of 40000 (INCI name: PEG-136/Steareth-100/HDI Copolymer).

According to another specific form of the present invention, use will be made of a polyurethane/polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane/polyethers are sold in particular by the company Rohm & Haas under the names Aculyn 46® and Aculyn 44®.

Aculyn 46® having the INCI name: PEG-150/Stearyl Alcohol/SMDI Copolymer, is a polycondensate of polyethylene glycol comprising 150 or 180 mol of ethylene oxide, of stearyl alcohol and of methylenebis(4-cyclohexyl isocyanate) (SMDI) at 15% by weight in a matrix of maltodextrin (4%) and water (81%) (INCI name: PEG-150/Stearyl Alcohol/SMDI Copolymer).

Aculyn 44® (PEG-150/Decyl Alcohol/SMDI Copolymer) is a polycondensate of polyethylene glycol comprising 150 or 180 mol of ethylene oxide, of decyl alcohol and of methylenebis(4-cyclohexyl isocyanate) (SMD1) at 35% by weight in a mixture of propylene glycol (39%) and water (26%) (INCI name: PEG-150/Decyl Alcohol/SMDI Copolymer).

As the associative polyurethanes, it may be preferable to use a compound represented by the following formula (1):

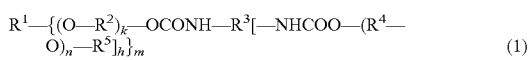

$$R^1-\{(O-R^2)_k-OCONH-R^3[-NHCOO-(R^4-O)_n-R^5]_h\}_m \quad (1)$$

wherein $R^1$ represents a hydrocarbon group, $R^2$ and $R^4$ independently represent alkylene groups having 2 to 4 carbon atoms, which alkylene groups may be identical or different from each other, or a phenylethylene group, $R^3$ represents a hydrocarbon group, which may optionally have a urethane bond, $R^5$ represents a branched chain or secondary hydrocarbon group, m represents a number of at least 2, h represents a number of at least 1, k represents a number within the range of 1 to 500, and n represents a number within the range of 1 to 200.

The hydrophobically modified polyurethane that is represented by the general formula (1) shown above is obtained by, for example, reacting at least one polyether polyol that is represented by the formula $R^1-[(O-R^2)_k-OH]_m$, at least one polyisocyanate that is represented by the formula $R^3-(NCO)_{h+1}$, and at least one polymonoalcohol that is represented by the formula $HO-(R^4-O)_n-R^5$.

In such cases, $R^1$ to $R^5$ in the general formula (1) are determined by the compounds $R^1-[(O-R^2)_k-OH]_m$, $R^3-(NCO)_{h+1}$ and $HO-(R^4-O)_n-R^5$. The loading ratios among the three compounds are not limited particularly and should preferably be such that the ratio of the isocyanate group derived from the polyisocyanate to the hydroxyl group derived from the polyether polyol and the polyether monoalcohol is selected within the range of NCO/OH of between 0.8:1 and 1.4:1.

The polyether polyol compound that is represented by the formula $R^1$—$[(O$—$R^2)_k$—$OH]_m$ and that may be used preferably for obtaining the associative polymer represented by the general formula (1) may be obtained from addition polymerization of an m-hydric polyol with an alkylene oxide, such as ethylene oxide, propylene oxide, butylene oxide, or epichlorohydrin, or with styrene oxide, and the like.

The polyols should preferably be di- to octa-hydric polyols. Examples of the di- to octa-hydric polyols include dihydric alcohols, such as ethylene glycol, propylene glycol, butylene glycol, hexamethylene glycol, and neopenthyl glycol; trihydric alcohols, such as glycerol, trioxy isobutane, 1,2,3-butanetriol, 1,2,3-pentanetriol, 2-methyl-1,2,3-propanetiol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-pentanetriol, pentamethylglycerol, pentaglycerol, 1,2,4-butanetriol, 1,2,4-pentanetriol, trimethylolethane, and trimethylolpropane; tetrahydric alcohols, such as pentaerythritol, 1,2,3,4-pentanetetrol, 2,3,4,5-hexanetetrol, 1,2,4,5-pentanetetrol, and 1,3,4,5-hexanetetrol; pentahydric alcohols, such as adonitol, arabitol, and xylitol; hexahydric alcohols, such as dipentaerythritol, sorbitol, mannitol, and iditol; and octahydric alcohols, such as sucrose.

Also, $R^2$ is determined by the alkylene oxide, styrene oxide, or the like, which is subjected to the addition. Particularly, for availability and excellent effects, an alkylene oxide having 2 to 4 carbon atoms, or styrene oxide is preferable.

The alkylene oxide, styrene oxide, or the like, to be subjected to the addition may be subjected to single polymerization, or random polymerization or block polymerization of at least two members. The procedure for the addition may be a conventional procedure. Also, the polymerization degree k may be selected within the range of 0 to 1,000, preferably within the range of 1 to 500, and more preferably within the range of 10 to 200. Further, the ratio of the ethylene group occupying $R^2$ should preferably be within the range of 50 to 100 mass % with respect to the total quantity of $R^2$. In such cases, the associative polymer appropriate for the purposes of the present invention is obtained.

Furthermore, the molecular weight of the polyether polyol compound that is represented by the formula $R^1$—$[(O$—$R^2)_k$—$OH]_m$ should preferably be selected within the range of 500 to 100,000, and should more preferably be selected within the range of 1,000 to 50,000.

The polyisocyanate that is represented by the formula $R^3$—$(NCO)_{h+1}$ and that may be used preferably for obtaining the hydrophobically modified polyether urethane represented by the general formula (1) employed in accordance with the present invention is not limited particularly in so far as the polyisocyanate has at least two isocyanate groups in the molecule. Examples of the polyisocyanates include aliphatic diisocyanates, aromatic diisocyanates, alicyclic diisocyanates, biphenyl diisocyanate, phenylmethane diisocyanate, phenylmethane triisocyanate, and phenylmethane tetraisocyanate.

Also, it is possible to employ dimers and trimers (isocyanurate bonds) of the above-enumerated polyisocyanates. Further, it is possible to employ biuret obtained by a reaction with an amine.

Furthermore, it is possible to employ a polyisocyanate having a urethane bond obtained by a reaction of the aforesaid polyisocyanate compound and a polyol. As the polyol, di- to octa-hydric polyols are preferable, and the above-enumerated polyols are preferable. In cases where a tri- or higher-hydric polyisocyanate is used as the polyisocyanate that is represented by the formula $R^3$—$(NCO)_{n+1}$, it is preferable to employ the aforesaid polyisocyanate having the urethane bond.

The polyether monoalcohol that is represented by the formula $HO$—$(R^4$—$O)_n$—$R^5$ and that may be used preferably for obtaining the hydrophobically modified polyether urethane represented by the general formula (1) employed in accordance with the present invention is not limited particularly in so far as the polyether monoalcohol is a polyether of a straight chain, branched chain, or secondary monohydric alcohol. The polyether monoalcohol may be obtained by addition polymerization of the straight chain, branched chain, or secondary monohydric alcohol with an alkylene oxide, such as ethylene oxide, propylene oxide, butylene oxide, or epichlorohydrin, or with styrene oxide, and the like.

The compound represented by the general formula (1) may be produced by, for example, heating at a temperature of 80 to 90° C. for 1 to 3 hours and thereby causing a reaction to occur in the same manner as that in the ordinary reaction of a polyether and an isocyanate.

As the compound represented by the general formula (1), polyethyleneglycol-240/decyltetradeceth-20/hexamethylene diisocyanate copolymer is preferable. The polyethyleneglycol-240/decyltetradeceth-20/hexamethylene diisocyanate copolymer is referred to also as PEG-240/HDI copolymer bis-decyltetradeceth-20 ether.

According to the present invention, it is preferable that the associative polyurethane polymer be selected from Steareth-100/PEG-136/HDI Copolymer sold by the company Rheox under the name of Rheolate FX 1100, PEG-240/HDI Copolymer Bis-decyltetradeceth-20 ether sold by the company Asahi Denka under the name of Adekanol GT-700, and mixtures thereof.

The amount of the (f) associative polymer in the composition according to the present invention may be from 0.01 to 10% by weight, preferably from 0.1 to 5% by weight, and more preferably from 0.5 to 2% by weight, relative to the total weight of the composition.

[Optional Ingredients]

The composition according to the present invention may also comprise one or more standard cosmetic adjuvants chosen from, for example, fillers, lipophilic thickeners, softeners, humectants, opacifiers, stabilizers, emollients, silicones, antifoams, fragrances, preserving agents, surfactants, active agents, colouring agents, cationic polymers, propellants, or any other ingredient usually used in cosmetics and/or dermatology.

Needless to say, a person skilled in the art will take care to select the optional adjuvant(s) added to the composition according to the present invention such that the advantageous properties intrinsically associated with the composition according to the invention are not, or are not substantially, adversely affected by the envisaged addition.

The composition according to the present invention may preferably be used as a cosmetic composition. In particular, the composition according to the present invention may be intended for application onto the skin, scalp and/or lips, preferably the skin, and in particular the skin around eyes. Thus, the composition according to the present invention can be used for a cosmetic process for the skin.

The cosmetic composition may be a skin care or skin makeup composition, for instance a foundation, a concealer, an eye makeup such as an eye shadow, or a body makeup, in particular, a foundation to be applied to the face and/or the neck, or an eye makeup to be applied around eyes.

EXAMPLES

The present invention will be described in a more detailed manner by way of examples. However, these examples should not be construed as limiting the scope of the present invention. The examples below are presented as non-limiting illustrations in the field of the invention.

Examples 1 to 4 and Comparative Examples 1 to 5

[Preparations]

The following compositions according to Examples (Ex.) 1 to 4 and Comparative Examples (Comp. Ex.) 1 to 5, shown in Table 1, were prepared by mixing the components shown in Table 1. Specifically, the materials from "Water" to "Alcohol Denat." in Table 1 were mixed and homogenized at room temperature to form Phase A. Separately, "Mexomere PAS" to "Isohexadecane" in Table 1 were mixed at 70° C. After dissolving or dispersing "KRATON G1657 MS SQR 1111" to "Disteardimonium Hectorite (Bentone 38 VCG)", the mixture was cooled to room temperature to form Phase B. Phase B was added to Phase A, followed by homogenizing at room temperature. The numerical values for the amounts of the components shown in Table 1 are all based on "% by weight" as active raw materials.

KRATON G1701 EU SQR 1111: Hydrogenated Styrene/Isoprene Copolymer

[Evaluations]

Bulk Stability: Whether the emulsion according to Examples 1-4 and Comparative Examples 1-5 caused phase separation just after the preparation of the emulsion was evaluated by visual observation.

15 mg of each, as a sample, of Examples 1-4 and Comparative Examples 1-5 was applied onto the eyelid, and spread with the fingers to form a cosmetic film. Softness of film, adhesiveness on the skin and lasting effect were evaluated by panelists as follows.

Softness of Film: After drying the cosmetic film on the eyelid, the feeling to the touch of the cosmetic film with the fingers was evaluated with regard to softness.

Adhesiveness on Skin: During the application of the sample, whether the sample could be applied on the eyelid without being repelled to form a uniform and adhesive film was evaluated.

Lasting Effect: Whether there was a crease on the cosmetic film, and whether the shade by the cosmetic film did not pale out after 8 hours were evaluated.

The evaluation criteria for the bulk stability, softness of film, adhesiveness on the skin and lasting effect are as follows.

TABLE 1

| | Ex. 1 | Ex. 2 | Ex. 3 | Ex. 4 | Comp. Ex. 1 | Comp. Ex. 2 | Comp. Ex. 3 | Comp. Ex. 4 | Comp. Ex. 5 |
|---|---|---|---|---|---|---|---|---|---|
| Water | 68.20 | 68.20 | 68.20 | 68.20 | 64.20 | 72.20 | 68.20 | 66.95 | 68.20 |
| Butylene Glycol | 1.60 | 1.60 | 1.60 | 1.60 | 1.60 | 1.60 | 1.60 | 1.60 | 1.60 |
| Propylene Glycol | 2.80 | 2.80 | 2.80 | 2.80 | 2.80 | 2.80 | 2.80 | 2.80 | 2.80 |
| Hexylene Glycol | 1.60 | 1.60 | 1.60 | 1.60 | 1.60 | 1.60 | 1.60 | 1.60 | 1.60 |
| Disodium EDTA | 0.10 | 0.10 | 0.10 | 0.10 | 0.10 | 0.10 | 0.10 | 0.10 | 0.10 |
| Simulgel 600 | 2.20 | 2.20 | 2.20 | — | 2.20 | 2.20 | 2.20 | 2.20 | 2.20 |
| Simulgel FL | — | — | — | 2.20 | — | — | — | — | — |
| Silica | 1.00 | 1.00 | 1.00 | 1.00 | 1.00 | 1.00 | 1.00 | 1.00 | 1.00 |
| Mica (and) Iron Oxides (and) Iron Oxides (and) Titanium Dioxide | 9.20 | 9.20 | 9.20 | 9.20 | 9.20 | 9.20 | 9.20 | 9.20 | 9.20 |
| Mica (and) Iron Oxides (and) Titanium Dioxide | 0.80 | 0.80 | 0.80 | 0.80 | 0.80 | 0.80 | 0.80 | 0.80 | 0.80 |
| Phenoxyethanol | 0.50 | 0.50 | 0.50 | 0.50 | 0.50 | 0.50 | 0.50 | 0.50 | 0.50 |
| Alcohol Denat. | 6.00 | 6.00 | 6.00 | 6.00 | 6.00 | 6.00 | 6.00 | 6.00 | 6.00 |
| Mexomere PAS | 0.50 | 0.50 | 0.50 | 0.50 | — | 1.00 | 0.50 | 0.50 | 0.50 |
| KRATON G1657 MS SQR 1111 | 0.50 | 0.50 | — | 0.50 | 1.00 | — | — | — | — |
| KRATON G1701 EU SQR 1111 | — | — | 0.50 | — | — | — | — | — | — |
| Silica Dimethyl Silylate (Aerosil R 972) | — | — | — | — | — | — | 0.50 | — | — |
| Silica Silylate (Dow Corning VM-2270 Aerogel Fine Particles) | — | — | — | — | — | — | — | 0.50 | — |
| Disteardimonium Hectorite (Bentone 38 VCG) | — | — | — | — | — | — | — | — | 0.50 |
| Isododecane | 5.00 | 0.50 | 5.00 | 5.00 | 9.00 | 1.00 | 5.00 | 6.25 | 5.00 |
| Isohexadecane | — | 4.50 | — | — | — | — | — | — | — |
| Total | 100.00 | 100.00 | 100.00 | 100.00 | 100.00 | 100.00 | 100.00 | 100.00 | 100.00 |
| Bulk Stability | ⊚ | ⊚ | ⊚ | ⊚ | ⊚ | ⊚ | ⊚ | ⊚ | ○ |
| Softness of Film | ⊚ | ⊚ | ⊚ | ⊚ | ⊚ | △ | △ | ⊚ | ⊚ |
| Adhesiveness on Skin | ⊚ | ⊚ | ⊚ | ⊚ | ⊚ | △ | ○ | ⊚ | ⊚ |
| Lasting Effect | ⊚ | ○ | ⊚ | ⊚ | △ | △ | X | X | X |

Simulgel 600: Acrylamide/Sodium Acryloyldimethyltaurate Copolymer (and) Isohexadecane (and) Polysorbate 80

Simulgel FL: Hydroxyethyl Acrylate/Sodium Acryloyldimethyltaurate Copolymer (and) Polysorbate 60

Mexomere PAS: Acrylic Acid/Isobutyl Acrylate/Isobornyl Acrylate Copolymer

KRATON G1657 MS SQR 1111: Hydrogenated Styrene/Butadiene Copolymer

Evaluation Criteria
⊚ Very good
○ Good
△ Slightly Poor
X Poor

The results are shown in Table 1.

As shown in Table 1, Examples 1-4, which includes a combination of a hydrocarbon-based block polymer (KRATON G1657 MS SQR 1111 or KRATON G1701 EU SQR 1111) and a film-forming linear ethylenic polymer devoid of styrene (Mexomere PAS), are stable and can provide all the target cosmetic effects (soft cosmetic film, uniform adhesion to skin and long lasting effect).

On the other hand, Comparative Examples 1-5, which include either the hydrocarbon-based block polymer or the film-forming linear ethylenic polymer devoid of styrene, are stable but cannot provide all the target cosmetic effects.

Examples 5 to 7 and Comparative Examples 6 to 8

[Preparations]

The following compositions according to Examples (Ex.) 5 to 7 and Comparative Examples (Comp. Ex.) 6 to 8, shown in Table 2, were prepared by mixing the components shown in Table 2. Specifically, the materials from "Disodium EDTA" to "Water" in Table 2 were mixed and homogenized at room temperature to form Phase A. Separately, the materials from "Isohexadecane" to "Acrylic Acid/Isobutyl Acrylates/Isobornyl Acrylate Copolymer" in Table 2 were mixed and homogenized at room temperature to form Phase C. Also, the materials from "Silica" to "Mica (and) Iron Oxides (and) Titanium Dioxide" were mixed and homogenized at room temperature to form Phase D.

At a temperature of about 30° C., Phase A, Phase C and Phase D were mixed, and the obtained mixture was homogenized at 80° C. Then, the materials from "PEG-240/HDI Copolymer Bis-Decyltetradeceth-20 Ether" to "Sodium Acrylates Crosspolymer-2 (and) Water (and) Silica" in Table 2 were mixed and homogenized by stirring the mixture at 3000 rpm. Then, the obtained mixture was cooled to 30° C. Lastly, Alcohol Denat. (ethanol) was added to the mixture and homogenized at room temperature.

The numerical values for the amounts of the components shown in Table 2 are all based on "% by weight" as active raw materials.

[Evaluations]
(Formation of Noodles)

The same amount of each composition according to Examples 5-7 and Comparative Examples 6-8 was applied onto the eyelids of each of 4 panelists, and evaluated the formation of noodles (noodles imply the breaking of a film formed by the composition) in accordance with the evaluation criteria shown below.

Evaluation Criteria
⊚ Very good (no formation of noodles)
○ Good (very slight formation of noodles)
Δ Slightly Poor (slight formation of noodles)
X Poor (formation of noodles)
The results are shown in Table 2.
(Uniform Spreadability)

The same amount of each composition according to Examples 5-7 and Comparative Examples 6-8 was applied onto the eyelids of each of 4 panelists, and spread to evaluate the uniform spreadability (complete uniform spreadability is preferable) in accordance with the evaluation criteria shown below.

Evaluation Criteria
⊚ Very good (complete uniform spreadability)
○ Good (uniform spreadability)
Δ Slightly Poor (slight non-uniform spreadability)
X Poor (non-uniform spreadability)
The results are shown in Table 2.
(Adhesiveness)

The same amount of each composition according to Examples 5-7 and Comparative Examples 6-8 was applied onto the eyelids of each of 4 panelists, and spread to evaluate the adhesiveness in accordance with the evaluation criteria shown below.

Evaluation Criteria
⊚ Very good
○ Good

TABLE 2

|  | Ex. 5 | Ex. 6 | Ex. 7 | Comp. Ex. 6 | Comp. Ex. 7 | Comp. Ex. 8 |
| --- | --- | --- | --- | --- | --- | --- |
| Disodium EDTA | 0.1 | 0.1 | 0.1 | 0.1 | 0.1 | 0.1 |
| Propylene Glycol | 2.8 | 2.8 | 2.8 | 2.8 | 2.8 | 2.8 |
| Phenoxyethanol | 0.5 | 0.5 | 0.5 | 0.5 | 0.5 | 0.5 |
| Hexylene Glycol | 1.6 | 1.6 | 1.6 | 1.6 | 1.6 | 1.6 |
| Butylene Glycol | 1.6 | 1.6 | 1.6 | 1.6 | 1.6 | 1.6 |
| Water | qsp 100 | qsp 100 | qsp 100 | qsp 100 | qsp 100 | qsp 100 |
| Isohexadecane | 4.5 | 4.5 | 4.5 | 4.5 | 4.5 | 4.5 |
| Acrylamides/Sodium Acryloyldimethyltaurate Copolymer (and) Isohexadecane (and) Polysorbate 80 | 2.2 | 2.2 | 2.2 | 2.2 | 2.2 | 2.2 |
| Hydrogenated Styrene/Isoprene Copolymer | 0.5 | 0.5 | 0.5 | 0.5 | 0.5 | 0.5 |
| Acrylic Acid/Isobutyl Acrylates/Isobornyl Acrylate Copolymer | 1 | 1 | 1 | 1 | 1 | 1 |
| Mica (and) Iron Oxides (and) Titanium Dioxide | 1 | 1 | 1 | 1 | 1 | 1 |
| Silica | 1 | 1 | 1 | 1 | 1 | 1 |
| Mica (and) Iron Oxides (and) Iron Oxides (and) Titanium Dioxide | 9.2 | 9.2 | 9.2 | 9.2 | 9.2 | 9.2 |
| Mica (and) Iron Oxides (and) Titanium Dioxide | 0.8 | 0.8 | 0.8 | 0.8 | 0.8 | 0.8 |
| PEG-240/HDI Copolymer Bis-Decyltetradeceth-20 Ether | 0.9 | 0.6 | 1.35 | — | — | — |
| Agar | — | — | — | — | — | 3 |
| Sodium Acrylates Crosspolymer-2 (and) Water (and) Silica | — | — | — | — | 0.3 | — |
| Alcohol Denat. | 6 | 6 | 6 | 6 | 6 | 6 |
| Formation of Noodles | ⊚ | ⊚ | ⊚ | ○ | X | ○ |
| Uniform Spreadability | ⊚ | ⊚ | ⊚ | ○ | ○ | X |
| Adhesiveness | ⊚ | ⊚ | ⊚ | ○ | X | Δ |
| Appearance | Gel | Gel | Gel | Cream | Gel | Gel |
| Ease of Dispensing Specific Amount | Good | Good | Good | Not Good | Good | Good |

Δ Slightly Poor
X Poor

The results are shown in Table 2.

(Appearance)

The appearance of each composition according to Examples 5-7 and Comparative Examples 6-8 was visually evaluated.

(Ease of Dispensing Specific Amount)

Each of the compositions according to Examples 5-7 and Comparative Examples 6-8 was dispensed by the finger from a container including the composition by a tester. The tester was requested to dispense a specific target amount of the composition from the container. The amount of the composition on the finger was weighed, and the difference between the specific target amount and the weight of the composition dispensed from the container was determined. This operation was repeated 5 times. If all the differences were within ±0.4 g, the composition was evaluated as "Good". If any of the differences was not within ±0.4 g, the composition was evaluated as "Not Good".

The invention claimed is:

1. A composition in the form of an oil-in-water emulsion, comprising:
   (a) at least one hydrocarbon-based block copolymer comprising at least one styrene block and at least one block comprising units chosen from butadiene, ethylene, propylene, butylene, isoprene, or mixtures thereof, which are optionally hydrogenated;
   (b) at least one film-forming linear ethylenic polymer devoid of styrene;
   (c) at least one oil; and
   (d) water,
   wherein the at least one film-forming linear ethylenic polymer devoid of styrene is an acrylic acid/isobutyl acrylate/isobornyl acrylate copolymer.

2. The composition of claim 1, wherein the at least one hydrocarbon-based block copolymer is chosen from styrene-ethylene/propylene, styrene-ethylene/butadiene, styrene-ethylene/butylene diblock copolymers, which are optionally hydrogenated, styrene-ethylene/propylene-styrene, styrene-ethylene/butadiene-styrene, styrene-isoprene-styrene and styrene-butadiene-styrene triblock copolymers, which are optionally hydrogenated, or mixtures thereof.

3. The composition of claim 1, wherein the at least one hydrocarbon-based block copolymer is chosen from a hydrogenated styrene/butadiene copolymer, a hydrogenated styrene/isoprene copolymer, or mixtures thereof.

4. The composition of claim 1, wherein the at least one hydrocarbon-based block copolymer is present in an amount ranging from about 0.01% to about 10% by weight, relative to the total weight of the composition.

5. The composition of claim 1, wherein the at least one hydrocarbon-based block copolymer is present in an amount ranging from about 0.1 to about 2% by weight, relative to the total weight of the composition.

6. The composition of claim 1, wherein the at least one film-forming linear ethylenic polymer devoid of styrene is present in an amount ranging from about 0.01% to about 10% by weight, relative to the total weight of the composition.

7. The composition of claim 1, wherein the at least one film-forming linear ethylenic polymer devoid of styrene is present in an amount ranging from about 0.1% to about 2% by weight, relative to the total weight of the composition.

8. The composition of claim 1, wherein the at least one oil is present in an amount ranging from about 0.1% to about 20% by weight, relative to the total weight of the composition.

9. The composition of claim 1, wherein the at least one oil is present in an amount ranging from about 1% to about 10% by weight, relative to the total weight of the composition.

10. The composition of claim 1, further comprising at least one hydrophilic thickener.

11. The composition of claim 1, further comprising at least one associative polymer.

* * * * *